(12) United States Patent
Altarac et al.

(10) Patent No.: US 11,304,817 B2
(45) Date of Patent: Apr. 19, 2022

(54) EXPANDABLE INTERBODY SPACER

(71) Applicant: NeuroStructures, Inc., Irvine, CA (US)

(72) Inventors: Moti Altarac, Irvine, CA (US); Joey Reglos, Irvine, CA (US)

(73) Assignee: Neurostructures, Inc., Irvine, CA (US)

( * ) Notice: Subject to any disclaimer, the term of this patent is extended or adjusted under 35 U.S.C. 154(b) by 0 days.

(21) Appl. No.: 16/894,308

(22) Filed: Jun. 5, 2020

(65) Prior Publication Data
US 2021/0378832 A1 Dec. 9, 2021

(51) Int. Cl.
*A61F 2/44* (2006.01)
*A61F 2/46* (2006.01)
*A61F 2/30* (2006.01)

(52) U.S. Cl.
CPC ............. *A61F 2/442* (2013.01); *A61F 2/447* (2013.01); *A61F 2/4611* (2013.01); *A61F 2002/30593* (2013.01); *A61F 2002/30904* (2013.01)

(58) Field of Classification Search
CPC ........ A61F 2/442; A61F 2/447; A61F 2/4611; A61F 2002/30593; A61F 2002/30904
USPC ...................... 623/17.11–17.16; 606/279, 99
See application file for complete search history.

(56) References Cited

U.S. PATENT DOCUMENTS

| | | |
|---|---|---|
| 3,554,075 A | 1/1971 | Johnson |
| 3,741,205 A | 6/1973 | Markolf et al. |
| 5,085,660 A | 2/1992 | Lin |
| 5,364,399 A | 11/1994 | Lowery et al. |
| 5,423,826 A | 6/1995 | Coates et al. |
| 5,549,612 A | 8/1996 | Yapp et al. |
| 5,616,142 A | 4/1997 | Yuan et al. |
| 5,616,144 A | 4/1997 | Yapp et al. |
| 5,676,483 A | 10/1997 | Koubek |
| 5,725,588 A | 3/1998 | Errico et al. |
| 6,045,552 A | 4/2000 | Zucherman et al. |
| 6,070,294 A | 6/2000 | Perkins et al. |
| 6,139,550 A | 10/2000 | Michelson |
| 6,258,089 B1 | 7/2001 | Campbell et al. |
| 6,261,291 B1 | 7/2001 | Talaber et al. |
| 6,398,783 B1 | 6/2002 | Michelson |
| 6,527,776 B1 | 3/2003 | Michelson |
| 6,599,290 B2 | 7/2003 | Bailey et al. |
| 6,602,255 B1 | 8/2003 | Campbell et al. |
| 6,605,090 B1 | 8/2003 | Trieu et al. |
| 6,626,907 B2 | 9/2003 | Campbell et al. |
| 6,629,998 B1 | 10/2003 | Lin |
| 6,652,525 B1 | 11/2003 | Assaker et al. |
| 6,695,846 B2 | 2/2004 | Richelsoph et al. |

(Continued)

FOREIGN PATENT DOCUMENTS

| | | |
|---|---|---|
| EP | 1520545 B1 | 11/2006 |
| EP | 1429675 B1 | 10/2007 |

(Continued)

*Primary Examiner* — Jessica Weiss
(74) *Attorney, Agent, or Firm* — Lukas IP; Rimas Lukas

(57) ABSTRACT

An expandable interbody spacer for the spine is provided. The interbody spacer includes a housing, upper and lower endplates, an anterior actuator, a posterior actuator, an anterior drive screw, and a posterior drive screw. The anterior and posterior drive screws are independently or simultaneously rotated with respect to each other by a driver to wedge one or more of the anterior and posterior actuators between the endplates moving them into parallel and/or angular expansion.

34 Claims, 23 Drawing Sheets

(56) References Cited

U.S. PATENT DOCUMENTS

| | | |
|---|---|---|
| 6,743,256 B2 | 6/2004 | Mason |
| 6,755,833 B1 | 6/2004 | Paul et al. |
| 6,793,658 B2 | 9/2004 | LeHuec et al. |
| 6,849,093 B2 | 2/2005 | Michelson |
| 6,926,718 B1 | 8/2005 | Michelson |
| 6,936,051 B2 | 8/2005 | Michelson |
| 6,964,664 B2 | 11/2005 | Freid et al. |
| 7,008,426 B2 | 3/2006 | Paul |
| 7,070,599 B2 | 7/2006 | Paul |
| 7,175,623 B2 | 2/2007 | Thramann et al. |
| 7,186,254 B2 | 3/2007 | Dinh et al. |
| 7,204,837 B2 | 4/2007 | Paul |
| 7,220,263 B2 | 5/2007 | Cordaro |
| 7,255,699 B2 | 8/2007 | Paul |
| 7,273,481 B2 | 9/2007 | Lombardo et al. |
| 7,276,070 B2 | 10/2007 | Muckter |
| 7,278,997 B1 | 10/2007 | Mueller et al. |
| 7,288,094 B2 | 10/2007 | Lindemann et al. |
| 7,288,095 B2 | 10/2007 | Baynham et al. |
| 7,291,152 B2 | 11/2007 | Abdou |
| 7,306,605 B2 | 12/2007 | Ross |
| 7,318,825 B2 | 1/2008 | Butler et al. |
| 7,322,984 B2 | 1/2008 | Doubler et al. |
| 7,438,715 B2 | 10/2008 | Doubler et al. |
| 7,452,370 B2 | 11/2008 | Anderson |
| 7,468,069 B2 | 12/2008 | Baynham et al. |
| 7,524,325 B2 | 4/2009 | Khalili |
| 7,601,170 B2 | 10/2009 | Winslow et al. |
| 7,651,517 B2 | 1/2010 | Konieczynski et al. |
| 7,662,154 B2 | 2/2010 | Ribeiro |
| 7,662,174 B2 | 2/2010 | Doubler et al. |
| 7,686,806 B2 | 3/2010 | Rhyne |
| 7,704,255 B2 | 4/2010 | Michelson |
| 7,740,630 B2 | 6/2010 | Michelson |
| 7,740,649 B2 | 6/2010 | Mosca et al. |
| 7,803,157 B2 | 9/2010 | Michelson |
| 7,811,285 B2 | 10/2010 | Michelson |
| 7,815,666 B2 | 10/2010 | Baynham et al. |
| 7,824,432 B2 | 11/2010 | Michelson |
| 7,857,839 B2 | 12/2010 | Duong et al. |
| 7,887,547 B2 | 2/2011 | Campbell et al. |
| 7,909,859 B2 | 3/2011 | Mosca et al. |
| 7,963,981 B2 | 6/2011 | Binder et al. |
| 7,985,242 B2 | 7/2011 | Forton et al. |
| 8,048,075 B2 | 11/2011 | Michelson |
| 8,057,522 B2 | 11/2011 | Rothman et al. |
| RE43,008 E | 12/2011 | Talaber et al. |
| 8,128,668 B2 | 3/2012 | Paul |
| 8,206,293 B2 | 6/2012 | Reglos et al. |
| 8,221,476 B2 | 7/2012 | Paul |
| 8,236,033 B2 | 8/2012 | Paul |
| 8,236,034 B2 | 8/2012 | Binder et al. |
| 8,394,145 B2 | 3/2013 | Weiman |
| 8,398,713 B2 | 3/2013 | Weiman |
| 8,419,777 B2 | 4/2013 | Walker et al. |
| 8,439,924 B1 | 5/2013 | McBride et al. |
| 8,460,308 B2 | 6/2013 | Marino et al. |
| 8,480,747 B2 | 7/2013 | Melkent et al. |
| 8,562,655 B2 | 10/2013 | Butler |
| 8,562,656 B2 | 10/2013 | Humphreys |
| 8,591,556 B2 | 11/2013 | Hansell et al. |
| 8,652,182 B1 | 2/2014 | Walker et al. |
| 8,668,723 B2 | 3/2014 | Altarac et al. |
| 8,845,731 B2 | 9/2014 | Weiman |
| 8,845,734 B2 | 9/2014 | Weiman |
| 8,852,279 B2 | 10/2014 | Weiman |
| 8,888,854 B2 | 11/2014 | Glerum et al. |
| 9,125,757 B2 | 9/2015 | Weiman |
| 9,204,972 B2 | 12/2015 | Weiman et al. |
| 9,204,974 B2 | 12/2015 | Glerum et al. |
| 9,233,007 B2 | 1/2016 | Sungarian et al. |
| 9,326,861 B2 | 5/2016 | Iott et al. |
| 9,381,093 B1 | 7/2016 | Morris et al. |
| 9,402,739 B2 | 8/2016 | Weiman et al. |
| 9,480,579 B2 | 11/2016 | Davenport et al. |
| 9,554,918 B2 | 1/2017 | Weiman |
| 9,561,116 B2 | 2/2017 | Weiman et al. |
| 9,743,958 B2 | 8/2017 | Ishii et al. |
| 9,770,343 B2 | 9/2017 | Weiman |
| 9,782,265 B2 | 10/2017 | Weiman et al. |
| 9,788,970 B2 | 10/2017 | Reimels |
| 9,801,734 B1 | 10/2017 | Stein et al. |
| 9,833,336 B2 | 12/2017 | Davenport et al. |
| 9,855,151 B2 | 1/2018 | Weiman |
| 9,867,715 B2 | 1/2018 | McLaughlin et al. |
| 9,907,673 B2 | 3/2018 | Weiman et al. |
| 9,913,726 B2 | 3/2018 | Weiman |
| 9,925,062 B2 | 3/2018 | Glerum et al. |
| 9,962,271 B2 | 5/2018 | Glerum |
| 9,968,462 B2 | 5/2018 | Weiman |
| 10,004,607 B2 | 6/2018 | Weiman et al. |
| 10,010,430 B2 | 7/2018 | Glerum et al. |
| 10,016,224 B2 | 7/2018 | Altarac et al. |
| 10,016,282 B2 | 7/2018 | Seifert et al. |
| 10,022,241 B2 | 7/2018 | Faulhaber et al. |
| 10,028,842 B2 | 7/2018 | Gray et al. |
| 10,052,213 B2 | 8/2018 | Glerum et al. |
| 10,052,215 B2 | 8/2018 | Hessler et al. |
| 10,080,669 B2 | 9/2018 | Davenport et al. |
| 10,085,849 B2 | 10/2018 | Weiman et al. |
| 10,117,754 B2 | 11/2018 | Davenport et al. |
| 10,137,001 B2 | 11/2018 | Weiman |
| 10,137,009 B2 | 11/2018 | Weiman et al. |
| 10,143,569 B2 | 12/2018 | Weiman et al. |
| 10,154,912 B2 | 12/2018 | Glerum |
| 10,219,913 B2 | 3/2019 | Matthews et al. |
| 10,219,914 B2 | 3/2019 | Faulhaber |
| 10,226,358 B2 | 3/2019 | Glerum |
| 10,226,359 B2 | 3/2019 | Glerum et al. |
| 10,265,190 B2 | 4/2019 | Faulhaber |
| 10,278,830 B1 | 5/2019 | Walker et al. |
| 10,299,934 B2 | 5/2019 | Seifert et al. |
| 10,314,719 B2 | 6/2019 | Hessler et al. |
| 10,327,917 B2 | 6/2019 | Glerum et al. |
| 10,350,081 B2 | 7/2019 | Seifert et al. |
| 10,350,085 B2 | 7/2019 | Glerum et al. |
| 10,369,000 B2 | 8/2019 | McLaughlin et al. |
| 10,369,002 B2 | 8/2019 | Rhoda et al. |
| 10,369,004 B2 | 8/2019 | Faulhaber |
| 10,376,377 B2 | 8/2019 | Seifert et al. |
| 10,390,962 B2 | 8/2019 | Weiman |
| 10,470,894 B2 | 11/2019 | Foley et al. |
| 10,492,928 B2 | 12/2019 | Himmelberger et al. |
| 10,500,057 B2 | 12/2019 | McLaughlin et al. |
| 10,524,924 B2 | 1/2020 | Davenport et al. |
| 10,548,743 B2 | 2/2020 | Faulhaber |
| 10,617,533 B2 | 4/2020 | Glerum et al. |
| 10,624,761 B2 | 4/2020 | Davenport et al. |
| 10,639,166 B2 | 5/2020 | Weiman et al. |
| 2002/0120270 A1 | 8/2002 | Trieu et al. |
| 2003/0060828 A1 | 3/2003 | Michelson |
| 2003/0093082 A1 | 5/2003 | Campbell et al. |
| 2003/0105462 A1 | 6/2003 | Haider |
| 2003/0105466 A1 | 6/2003 | Ralph et al. |
| 2003/0105467 A1 | 6/2003 | Ralph et al. |
| 2003/0125739 A1 | 7/2003 | Bagga et al. |
| 2003/0135216 A1 | 7/2003 | Sevrain |
| 2003/0153920 A1 | 8/2003 | Ralph et al. |
| 2003/0171753 A1 | 9/2003 | Collins et al. |
| 2003/0181912 A1 | 9/2003 | Michelson |
| 2003/0187440 A1 | 10/2003 | Richelsoph et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0229348 A1 | 12/2003 | Sevrain |
| 2003/0236528 A1 | 12/2003 | Thramann |
| 2004/0006343 A1 | 1/2004 | Sevrain |
| 2004/0015169 A1 | 1/2004 | Gause |
| 2004/0019353 A1 | 1/2004 | Freid et al. |
| 2004/0024081 A1 | 2/2004 | Trieu et al. |
| 2004/0030336 A1 | 2/2004 | Khanna |
| 2004/0034352 A1 | 2/2004 | Needham et al. |

(56) References Cited

U.S. PATENT DOCUMENTS

| | | |
|---|---|---|
| 2004/0039387 A1 | 2/2004 | Gause et al. |
| 2004/0049279 A1 | 3/2004 | Sevrain |
| 2004/0068319 A1 | 4/2004 | Cordaro |
| 2004/0087945 A1 | 5/2004 | Ralph et al. |
| 2004/0087951 A1 | 5/2004 | Khalili |
| 2004/0092929 A1 | 5/2004 | Zindrick |
| 2004/0092947 A1 | 5/2004 | Foley |
| 2004/0097925 A1 | 5/2004 | Boehm, Jr. et al. |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097950 A1 | 5/2004 | Foley et al. |
| 2004/0106924 A1 | 6/2004 | Ralph et al. |
| 2004/0122426 A1 | 6/2004 | Michelson |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0133205 A1 | 7/2004 | Thramann et al. |
| 2004/0153088 A1 | 8/2004 | Ralph et al. |
| 2004/0158246 A1 | 8/2004 | Assaker et al. |
| 2004/0177847 A1 | 9/2004 | Foley et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204710 A1 | 10/2004 | Patel et al. |
| 2004/0204712 A1 | 10/2004 | Kolb et al. |
| 2004/0204713 A1 | 10/2004 | Abdou |
| 2004/0210314 A1 | 10/2004 | Michelson |
| 2004/0215192 A1 | 10/2004 | Justis et al. |
| 2004/0215195 A1 | 10/2004 | Shipp et al. |
| 2004/0220571 A1 | 11/2004 | Assaker et al. |
| 2004/0220572 A1 | 11/2004 | Michelson |
| 2004/0225290 A1 | 11/2004 | Ferree |
| 2004/0236333 A1 | 11/2004 | Lin |
| 2004/0236334 A1 | 11/2004 | Michelson |
| 2004/0236335 A1 | 11/2004 | Michelson |
| 2004/0243128 A1 | 12/2004 | Howland |
| 2004/0260306 A1 | 12/2004 | Fallin et al. |
| 2005/0015092 A1 | 1/2005 | Rathbun et al. |
| 2005/0015093 A1 | 1/2005 | Suh et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038436 A1 | 2/2005 | Michelson |
| 2005/0043732 A1 | 2/2005 | Dalton |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0137597 A1 | 6/2005 | Butler et al. |
| 2005/0149021 A1 | 7/2005 | Tozzi |
| 2005/0149026 A1 | 7/2005 | Butler et al. |
| 2005/0149027 A1 | 7/2005 | Campbell et al. |
| 2005/0171551 A1 | 8/2005 | Sukovich et al. |
| 2005/0177160 A1 | 8/2005 | Baynham et al. |
| 2005/0177161 A1 | 8/2005 | Baynham et al. |
| 2005/0177163 A1 | 8/2005 | Abdou |
| 2005/0187551 A1 | 8/2005 | Orbay et al. |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0208095 A1 | 9/2005 | Hunter et al. |
| 2005/0209593 A1 | 9/2005 | Kolb |
| 2005/0216005 A1 | 9/2005 | Howland |
| 2005/0216009 A1 | 9/2005 | Michelson |
| 2005/0216010 A1 | 9/2005 | Michelson |
| 2005/0228386 A1 | 10/2005 | Ziolo et al. |
| 2005/0234455 A1 | 10/2005 | Binder et al. |
| 2005/0261690 A1 | 11/2005 | Binder et al. |
| 2005/0273105 A1 | 12/2005 | Konieczynski et al. |
| 2005/0277930 A1 | 12/2005 | Parsons |
| 2005/0277938 A1 | 12/2005 | Parsons |
| 2005/0283152 A1 | 12/2005 | Lindemann et al. |
| 2006/0009845 A1 | 1/2006 | Chin |
| 2006/0030852 A1 | 2/2006 | Sevrain |
| 2006/0079961 A1 | 4/2006 | Michelson |
| 2006/0082015 A1 | 4/2006 | Happonen et al. |
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200146 A1 | 9/2006 | Doubler et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |
| 2006/0276792 A1 | 12/2006 | Ensign et al. |
| 2006/0287653 A1 | 12/2006 | Rhyne |
| 2007/0083203 A1 | 4/2007 | Ribeiro |
| 2007/0123884 A1 | 5/2007 | Abdou |
| 2007/0167954 A1 | 7/2007 | Sicvol et al. |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |
| 2007/0233110 A1 | 10/2007 | Muhanna et al. |
| 2007/0233117 A1 | 10/2007 | Butler et al. |
| 2007/0233118 A1 | 10/2007 | McLain |
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0051794 A1 | 2/2008 | Dec et al. |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0269806 A1 | 10/2008 | Zhang et al. |
| 2008/0287999 A1 | 11/2008 | Markworth |
| 2008/0288001 A1 | 11/2008 | Cawley et al. |
| 2009/0105831 A1 | 4/2009 | Jones et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1 | 7/2009 | Sanders et al. |
| 2009/0210008 A1 | 8/2009 | Butler et al. |

(56) References Cited

U.S. PATENT DOCUMENTS

| | | |
|---|---|---|
| 2009/0222049 A1 | 9/2009 | Frigg et al. |
| 2009/0259226 A1 | 10/2009 | Michelson |
| 2009/0270926 A1 | 10/2009 | Hawkes |
| 2010/0016901 A1 | 1/2010 | Robinson |
| 2010/0042159 A1 | 2/2010 | Butler |
| 2010/0049256 A1 | 2/2010 | Jeon et al. |
| 2010/0057206 A1 | 3/2010 | Duffield et al. |
| 2010/0069968 A1 | 3/2010 | Assaker et al. |
| 2010/0145459 A1 | 6/2010 | McDonough et al. |
| 2010/0234897 A1 | 9/2010 | Fisher et al. |
| 2010/0312279 A1 | 12/2010 | Gephart et al. |
| 2010/0312346 A1 | 12/2010 | Kueenzi et al. |
| 2011/0054528 A1 | 3/2011 | Michelson |
| 2011/0106159 A1 | 5/2011 | Nazeck |
| 2011/0118784 A1 | 5/2011 | Baynham et al. |
| 2011/0190770 A1 | 8/2011 | Suh |
| 2011/0213421 A1 | 9/2011 | Binder et al. |
| 2011/0230885 A1 | 9/2011 | Weiner et al. |
| 2011/0270311 A1 | 11/2011 | Assaker et al. |
| 2011/0313477 A1 | 12/2011 | McLean et al. |
| 2012/0065734 A1 | 3/2012 | Barrett et al. |
| 2012/0109208 A1 | 5/2012 | Justis et al. |
| 2012/0179259 A1 | 7/2012 | McDonough et al. |
| 2012/0245690 A1 | 9/2012 | Cowan, Jr. et al. |
| 2012/0277870 A1 | 11/2012 | Wolters et al. |
| 2013/0023936 A1 | 1/2013 | Altarac et al. |
| 2013/0046345 A1 | 2/2013 | Jones et al. |
| 2013/0053895 A1 | 2/2013 | Stoll et al. |
| 2013/0060294 A1 | 3/2013 | Donahue |
| 2013/0184767 A1 | 7/2013 | Kaufman et al. |
| 2013/0197588 A1 | 8/2013 | Abdou |
| 2013/0204306 A1 | 8/2013 | Walker et al. |
| 2013/0245705 A1 | 9/2013 | McBride et al. |
| 2013/0261679 A1 | 10/2013 | McBride et al. |
| 2013/0331892 A1 | 12/2013 | Peterson et al. |
| 2013/0345814 A1 | 12/2013 | Walkenhorst et al. |
| 2014/0142632 A1 | 5/2014 | Keyer et al. |
| 2014/0148860 A1 | 5/2014 | Rinner |
| 2014/0277145 A1 | 9/2014 | Reitblat et al. |
| 2014/0277206 A1 | 9/2014 | Reitblat et al. |
| 2014/0288653 A1* | 9/2014 | Chen ................... A61F 2/446 623/17.16 |
| 2014/0343678 A1* | 11/2014 | Suddaby ............. A61F 2/4611 623/17.16 |
| 2015/0039035 A1 | 2/2015 | Kruger |
| 2015/0094772 A1 | 4/2015 | Black et al. |
| 2016/0022317 A1 | 1/2016 | Kraus |
| 2016/0128746 A1 | 5/2016 | Dunaway |
| 2017/0367842 A1* | 12/2017 | Predick ............... A61F 2/4455 623/17.16 |
| 2017/0367844 A1 | 12/2017 | Eisen et al. |
| 2018/0318099 A1 | 11/2018 | Altarac et al. |
| 2019/0000644 A1 | 1/2019 | Moore et al. |
| 2019/0133779 A1* | 5/2019 | McLaughlin ........ A61F 2/4425 623/17.16 |
| 2019/0269521 A1* | 9/2019 | Shoshtaev ............ A61F 2/447 623/17.16 |
| 2019/0298524 A1* | 10/2019 | Lauf ................. A61F 2/30749 623/17.16 |
| 2020/0383797 A1* | 12/2020 | Predick ................ A61F 2/30 623/17.16 |
| 2021/0121299 A1* | 4/2021 | Hyder .................. A61F 2/447 623/17.16 |

FOREIGN PATENT DOCUMENTS

| | | | |
|---|---|---|---|
| EP | 1841376 A2 | 10/2007 | |
| EP | 1847229 A2 | 10/2007 | |
| FR | 2948553 A1 | 2/2011 | |
| KR | 20080105505 A | * 12/2008 | ............ A61F 2/4611 |
| WO | 2006076422 A2 | 7/2006 | |
| WO | 2006138291 A2 | 12/2006 | |
| WO | 2007037774 A1 | 4/2007 | |
| WO | 2007056516 A2 | 5/2007 | |
| WO | 2007101266 A1 | 9/2007 | |
| WO | 2007103081 A2 | 9/2007 | |
| WO | 2007121080 A2 | 10/2007 | |
| WO | 2006138291 B1 | 11/2007 | |
| WO | 2007134199 A2 | 11/2007 | |
| WO | 2009089395 A2 | 7/2009 | |
| WO | 2009091770 A1 | 7/2009 | |
| WO | 2009091775 A2 | 7/2009 | |

* cited by examiner

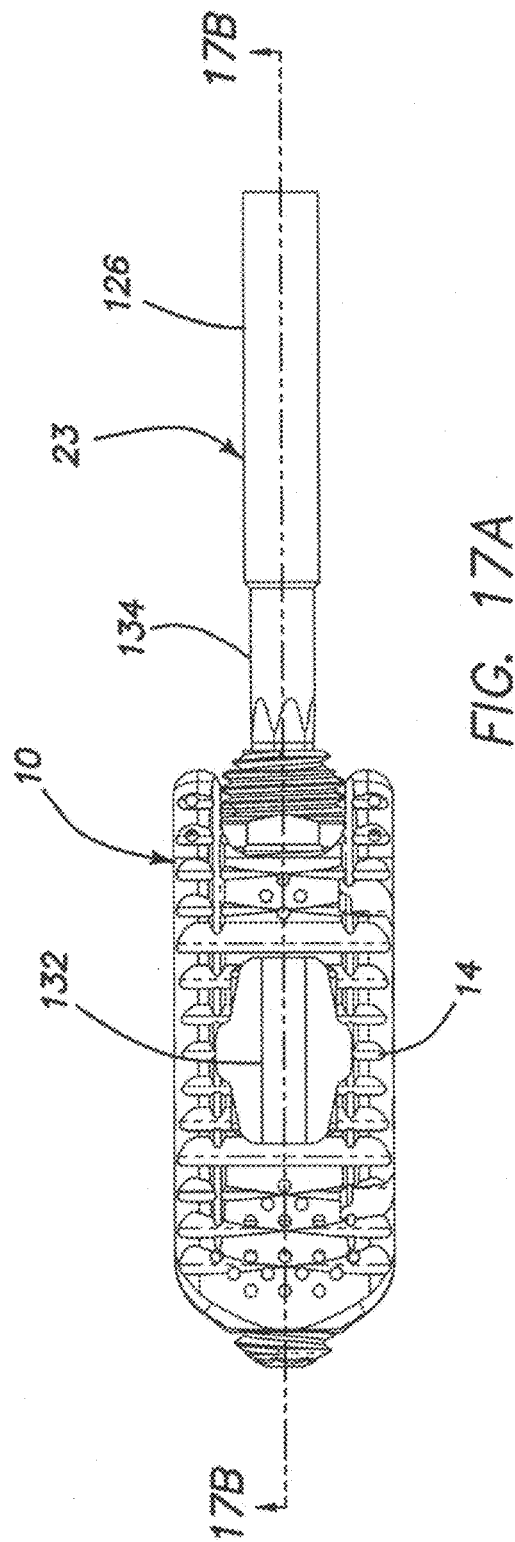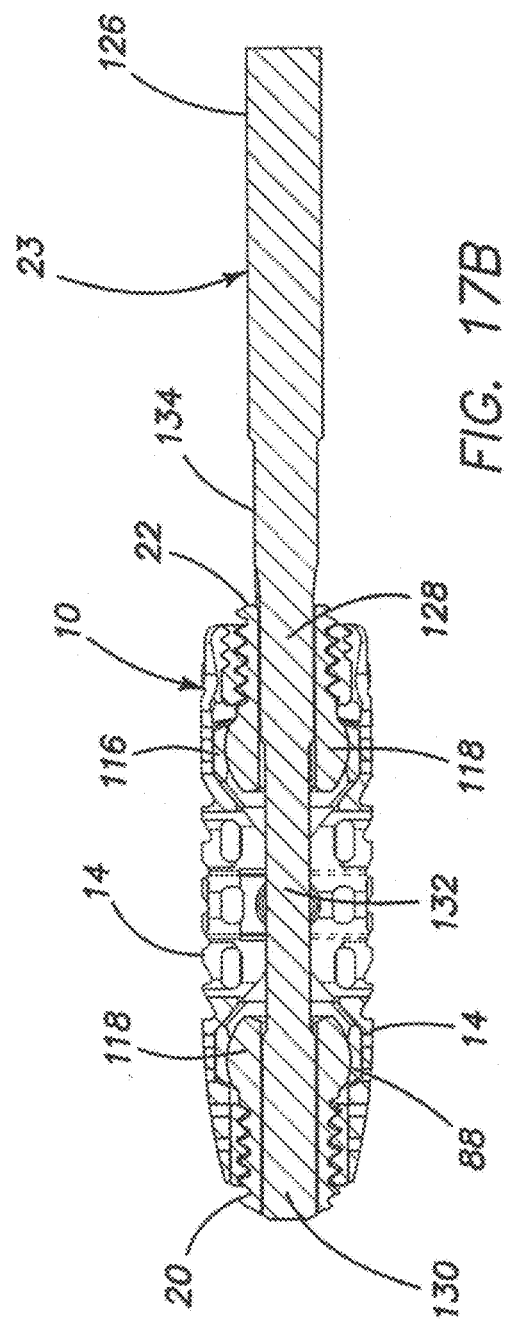

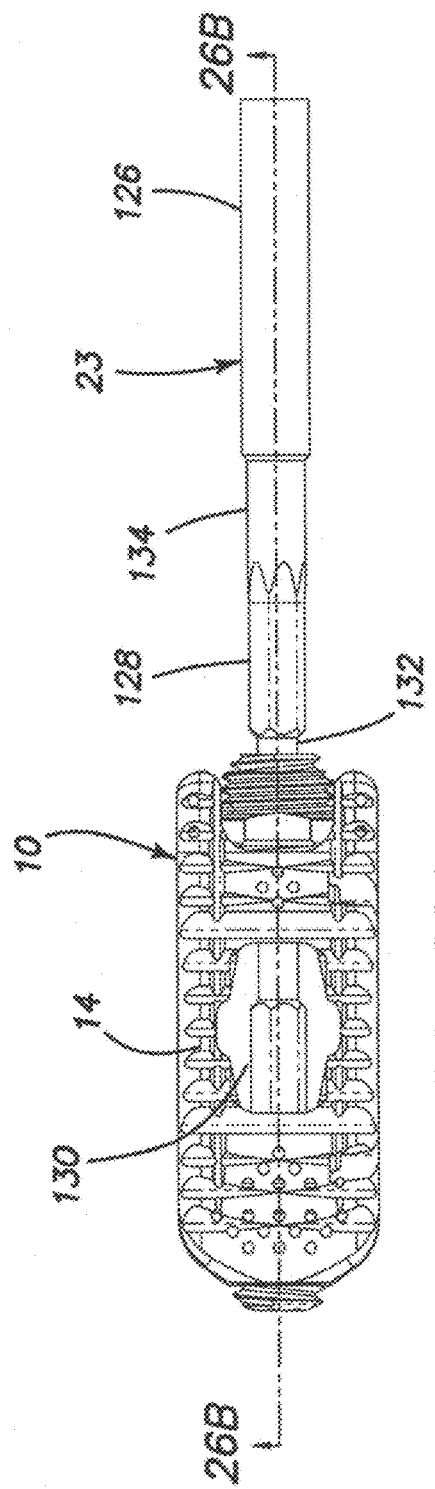
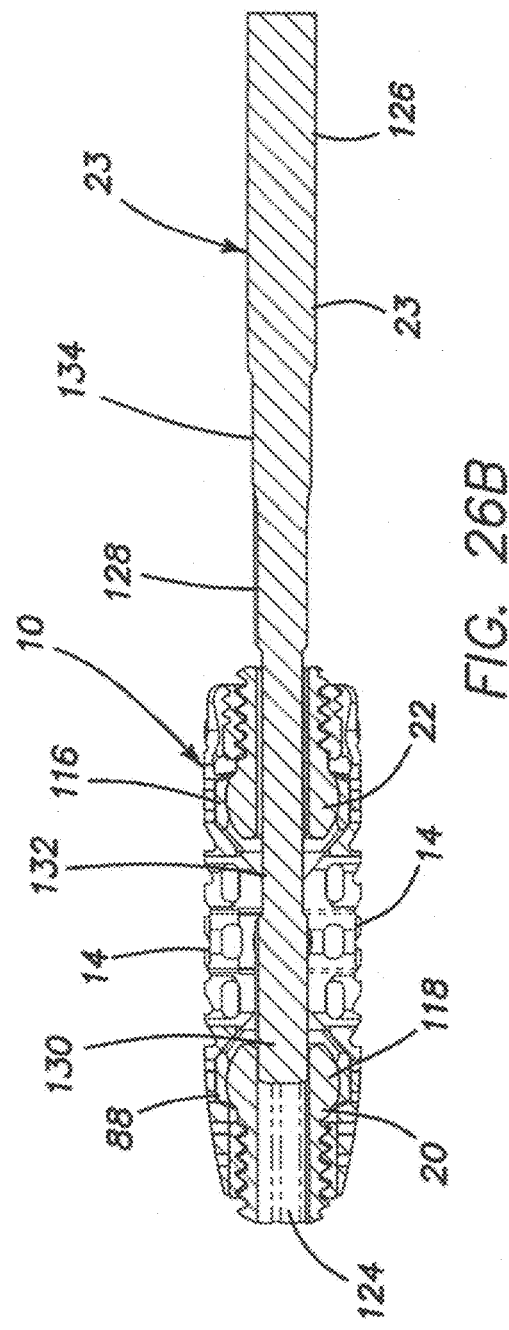
FIG. 26A
FIG. 26B

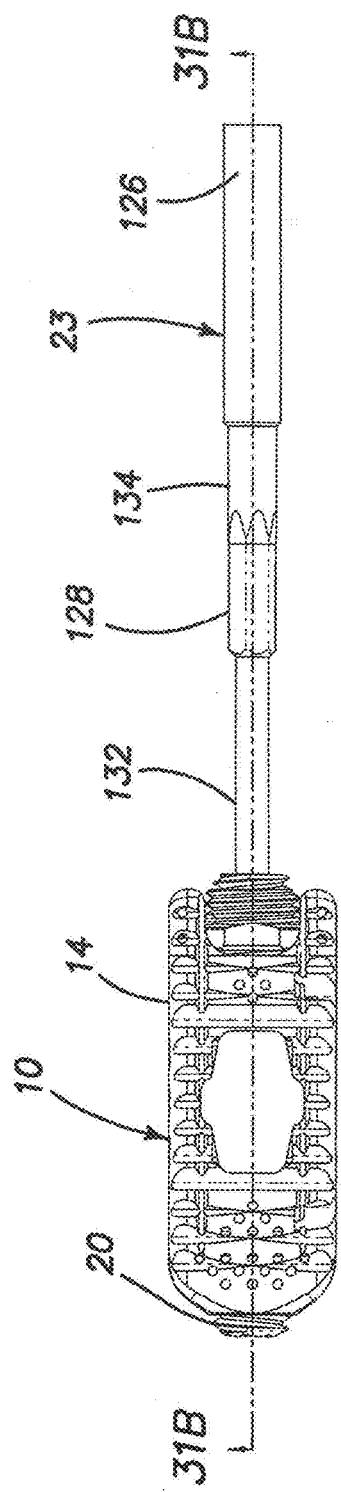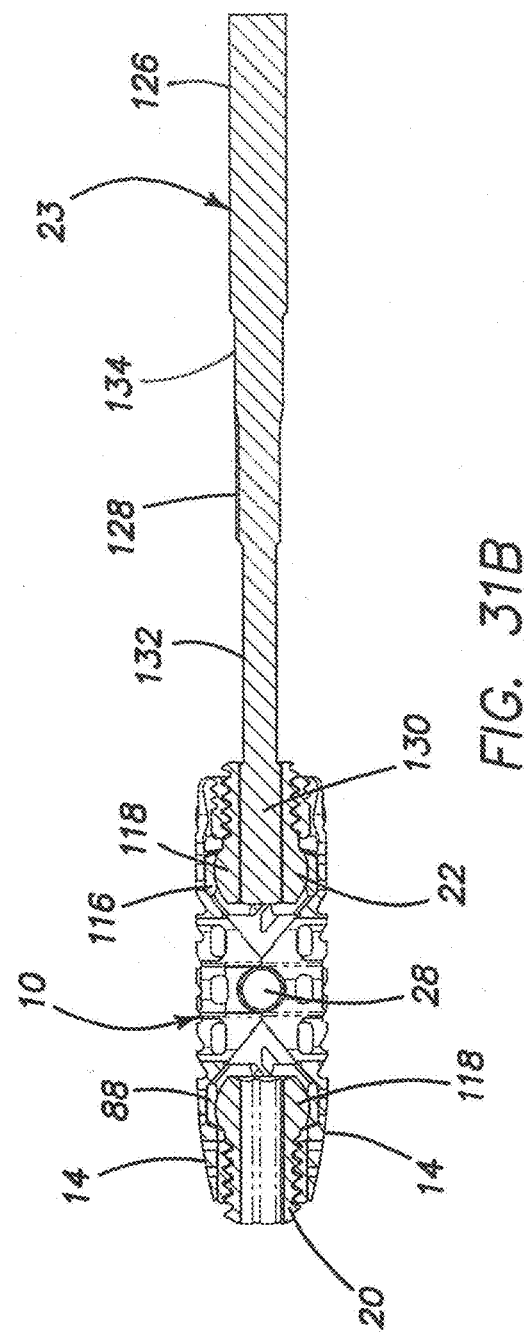
FIG. 31A
FIG. 31B

EXPANDABLE INTERBODY SPACER

FIELD OF THE INVENTION

This application relates generally to spinal implants, and in particular, expandable intervertebral spacers and fusion cages.

BACKGROUND OF THE INVENTION

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In a posterior lumbar interbody fusion (PLIF) surgery, spinal fusion is achieved in the lower back by inserting an implant such as a cage and typically graft material to encourage bone ingrowth directly into the disc space between adjacent vertebrae. The surgical approach for PLIF is from the back of the patient, posterior to the spinal column. An anterior lumbar interbody fusion (ALIF) surgical procedure is similar to the PLIF procedure except that in the ALIF procedure, the disc space is fused by approaching the spine through the abdomen from an anterior approach instead of from a posterior approach. Another fusion procedure is called a transforaminal lumbar interbody fusion (TLIF) which involves a posterior and lateral approach to the disc space. To gain access to the disc space, the facet joint may be removed whereby access is gained via the nerve foramen. In an extreme lateral interbody fusion (XLIF), the disc space is accessed from small incisions on the patient's side.

In the typical procedures described above, the adjacent vertebrae must be distracted apart by a substantial amount in order to allow the surgeon to advance the implant with relatively little resistance along the delivery path. Also, the surgeon must typically release the implant at least once as the implant is being delivered along the delivery path and align and position the implant at the target position of implantation, typically in the anterior aspect of the disc space. If static spacers having a fixed height are employed, the right-sized spacer is selected from a plurality of spacers. Sometimes the selected static spacer must be interchanged for one of a different height during the procedure. Expandable spacers provide several advantages over static spacers. For example, expandable spacers may be more easily inserted in their low-profile configuration and then mechanically expanded into their high-profile configuration when in the right position. Another advantage of some expandable spacers is that the degree of expansion easily can be adjusted in-situ according to the specific anatomy of the patient. Generally, expandable spacers avoid the need to stock multiple sizes, and to remove and replace spacers during the procedure.

There is a need to provide an expandable spacer that is capable of customized expansion given a wide variability in patient anatomy at each vertebral level that meets the surgeon's demands for providing the best stabilization solutions. Sometimes uniform parallel expansion of the spacer is required. Sometimes only distal or proximal angulation of the spacer is required and sometimes a combination of distal or proximal angulation together with parallel expansion is required. Therefore, there is a need to provide a new and improved expandable interbody spacer that is versatile in both angulation and parallel expansion, easy to position, deploy from a low-profile to a high-profile configuration, angulate both proximally and distally as well as expand uniformly. This invention, as described in the detailed description, sets forth an improved interbody spacer that meets these needs.

SUMMARY OF THE INVENTION

According to one aspect of the invention, an expandable interbody spacer for the spine is provided. The expandable interbody spacer includes a housing having two sides interconnected by a distal endwall and a proximal endwall defining a hollow interior. The distal endwall includes a threaded distal opening and the proximal endwall having a threaded proximal opening. The spacer includes an upper endplate and a lower endplate each having a posterior end and an anterior end, a bone-engaging surface and an interior surface opposite to the bone-engaging surface. The interior surface includes an anterior ramp surface extending at an angle with respect to the interior surface and a posterior ramp surface extending at an angle with respect to the interior surface. The spacer includes an anterior actuator located between the interior surfaces of the upper endplate and lower endplate near the distal end of the spacer. The anterior actuator includes an upper anterior actuator segment and a lower anterior actuator segment. The upper anterior actuator segment has a curved inner surface for contact with the anterior drive screw and an angled leading surface for contact with the anterior ramp surface of the upper endplate. The lower anterior actuator segment has a curved inner surface for contact with the anterior drive screw and an angled leading surface for contact with the anterior ramp surface of the lower endplate. The spacer includes a posterior actuator located between the interior surfaces of the upper endplate and lower endplate near the proximal end of the spacer. The posterior actuator includes an upper posterior actuator segment and a lower posterior actuator segment. The upper posterior actuator segment has a curved inner surface for contact with the posterior drive screw and an angled leading surface for contact with the posterior ramp surface of the upper endplate. The lower posterior actuator segment has a curved inner surface for contact with the posterior drive screw and an angled leading surface for contact with the posterior ramp surface of the lower endplate. The anterior drive screw includes a proximal ball head connected to a distal threaded shank. The ball head of the anterior drive screw is located between the curved inner surfaces of the upper and lower anterior actuator segments. The distal threaded shank is threadingly connected to the threaded distal opening. The anterior drive screw has an anterior drive bore extending from a proximal opening along a longitudinal drive axis. The spacer includes a posterior drive screw including a proximal threaded shank connected to a distal ball head. The ball head of the posterior drive screw is located between the curved inner surfaces of the upper and lower posterior actuator segments. The proximal threaded shank is threadingly connected to the threaded proximal opening. The posterior drive screw has a posterior drive bore extending along the longitudinal drive axis between a proximal opening in the threaded shank and a distal opening in the ball head. Rotation of the posterior drive screw in a first direction relative to the proximal end of the spacer around the drive axis translates the posterior drive screw distally to wedge apart and expand the distance between the posterior ends of the upper and lower endplates. Rotation of the anterior drive screw in the first direction relative to the proximal end of the spacer around the drive axis translates the anterior drive screw proximally to wedge apart the anterior ends of the upper and lower endplates. Rotation of the posterior drive screw in a second direction relative to the proximal end of the spacer around the drive axis translates the posterior drive screw proximally to reduce the distance between the posterior ends of the upper and lower endplates. Rotation of the anterior drive screw in the second direction relative to the proximal end of the spacer around the drive axis translates the anterior drive screw distally to reduce the distance between the anterior ends of the upper and lower endplates.

According to another aspect of the invention, a driver for an expandable interbody spacer having a proximal end and a distal end is provided. The driver includes a first drive portion having a first length extending along a longitudinal axis of the driver. The first drive portion has a first diameter and a non-circular cross-sectional first shape taken perpendicular to the longitudinal axis extending along the first length. The driver includes a second drive portion having a second length extending along the longitudinal axis. The second drive portion has a second diameter and a non-circular cross-sectional second shape taken perpendicular to the longitudinal axis extending along the second length. The driver includes a middle portion located between the first drive portion and the second drive portion. The middle portion has a middle length extending along the longitudinal axis. The middle portion has a middle diameter and a cross-sectional middle shape taken perpendicular to the longitudinal axis extending along the middle length. The driver includes a handle located at the proximal end. The handle has a handle length extending along the longitudinal axis and a handle diameter. The first drive portion extends from the distal end of the spacer to a distal end of the middle portion. The middle portion extends from a proximal end of the first drive portion to a distal end of the second drive portion. The handle extends from a proximal end of the second drive portion to the proximal end of the spacer.

According to another aspect of the invention, a method for an interbody spacer for the spine is provided. The method includes the step of providing an expandable interbody spacer having a longitudinal axis, a proximal end and a distal end. The spacer includes a housing having a threaded proximal opening and a threaded distal opening. The spacer includes an upper endplate having an anterior end and a posterior end. The upper endplate has an anterior angled surface and a posterior angled surface. The spacer includes a lower endplate having an anterior end and a posterior end. The lower endplate has an anterior angled surface and a posterior angled surface. The spacer includes an anterior drive screw threadingly connected to the distal opening. The anterior drive screw includes an anterior ball head connected to a threaded anterior shaft. The anterior drive screw includes an anterior drive bore having a bore diameter and a cross-sectional shape taken perpendicular to and extending along a longitudinal drive axis. The spacer includes an anterior actuator coupled to the anterior drive screw. The anterior actuator includes an upper drive surface for mating with the anterior angled surface of the upper endplate and a lower drive surface for mating with the anterior angled surface of the lower endplate. The spacer includes a posterior drive screw threadingly connected to the proximal opening. The posterior drive screw includes a posterior ball head connected to a threaded posterior shaft. The posterior drive screw includes a posterior drive bore having a bore diameter and cross-sectional shape taken perpendicular to and extending along the drive axis. The posterior drive bore is coaxially aligned with the anterior drive bore along the drive axis. The spacer includes a posterior actuator coupled to the posterior drive screw. The posterior actuator includes an upper drive surface for mating with the posterior angled surface of the upper endplate and a lower drive surface for mating the posterior angled surface of the lower endplate. The method includes the step of providing a driver having a longitudinal axis, a proximal end and a distal end. The driver includes a first drive portion having a first length extending along a longitudinal axis of the driver. The first drive portion has a first diameter and a non-circular cross-sectional first shape taken perpendicular to the longitudinal axis extending along the first length. The first shape is sized and configured to matingly engage the anterior drive bore and the posterior drive bore to rotate the anterior drive screw or posterior drive screw. The driver includes a second drive portion having a second length extending along the longitudinal axis; the second drive portion having a second diameter and a non-circular cross-sectional second shape taken perpendicular to the longitudinal axis extending along the second length. The second shape is sized and configured to matingly engage the posterior drive bore to rotate the posterior drive screw. The driver includes a middle portion located between the first drive portion and the second drive portion. The middle portion has a middle length extending along the longitudinal axis. The middle portion has a middle diameter and a cross-sectional middle shape taken perpendicular to the longitudinal axis extending along the middle length. The driver includes a handle located at the proximal end. The handle has a handle length extending along the longitudinal axis and a handle diameter. The first drive portion extends from the distal end of the spacer to a distal end of the middle portion. The middle portion extends from a proximal end of the first drive portion to a distal end of the second drive portion. The handle extends from a proximal end of the second drive portion to the proximal end of the driver.

BRIEF DESCRIPTION OF THE DRAWINGS

FIG. 17A is a top view of a driver engaged with an expandable spacer for parallel expansion according to the present invention.

FIG. 17B is a cross-sectional view of a driver engaged with an expandable spacer taken along line 17B-17B of FIG. 17A.

FIG. 26A is a top view of a driver engaged with an expandable spacer for anterior angular expansion according to the present invention.

FIG. 26B is cross-sectional view of a driver engaged with an expandable interbody spacer taken along line 26B-26B of FIG. 26A.

FIG. 31A is a top view of a driver engaged with an expandable spacer for posterior angular expansion according to the present invention.

FIG. 31B is cross-sectional view of a driver engaged with an expandable interbody spacer taken along line 31B-31B of FIG. 31A.

DETAILED DESCRIPTION OF THE INVENTION

Figure 1:
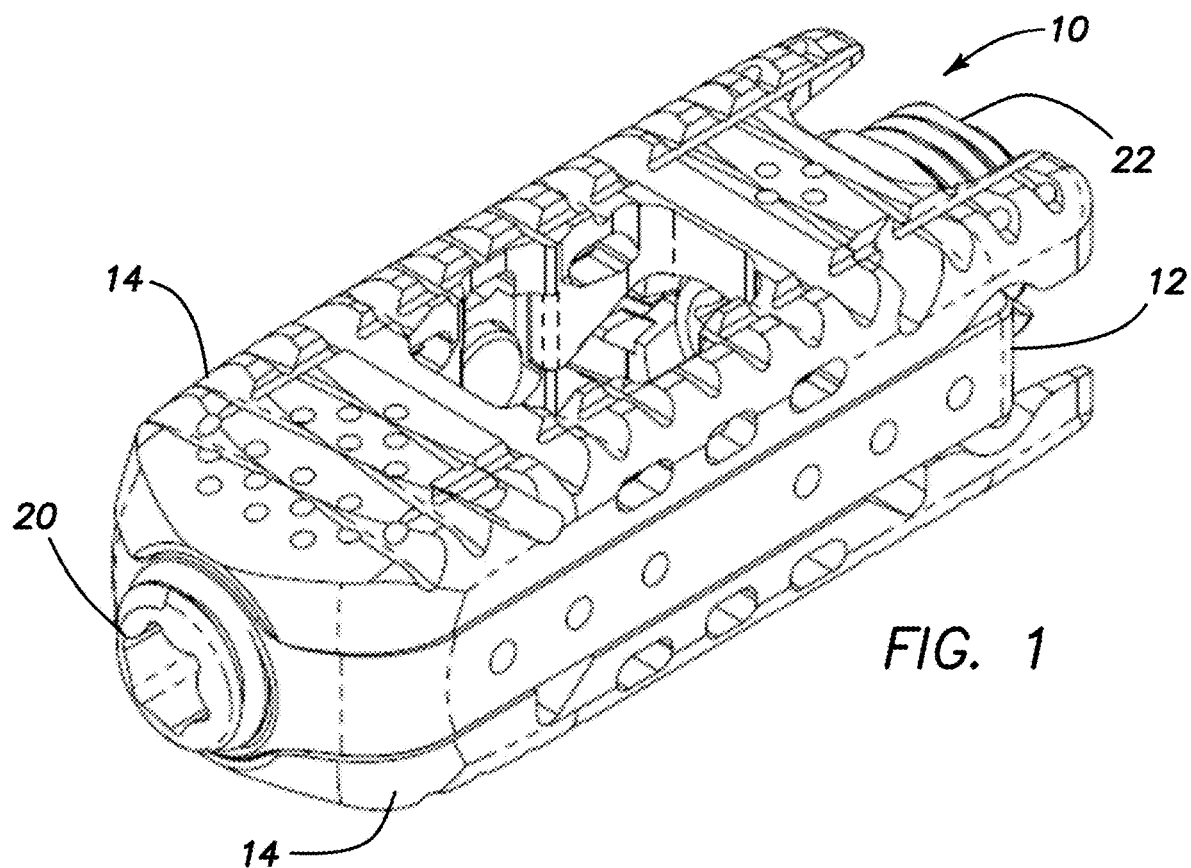
FIG. 1 is a front top perspective view of an expandable interbody spacer in its low-profile configuration according to the present invention.
Figure 2:
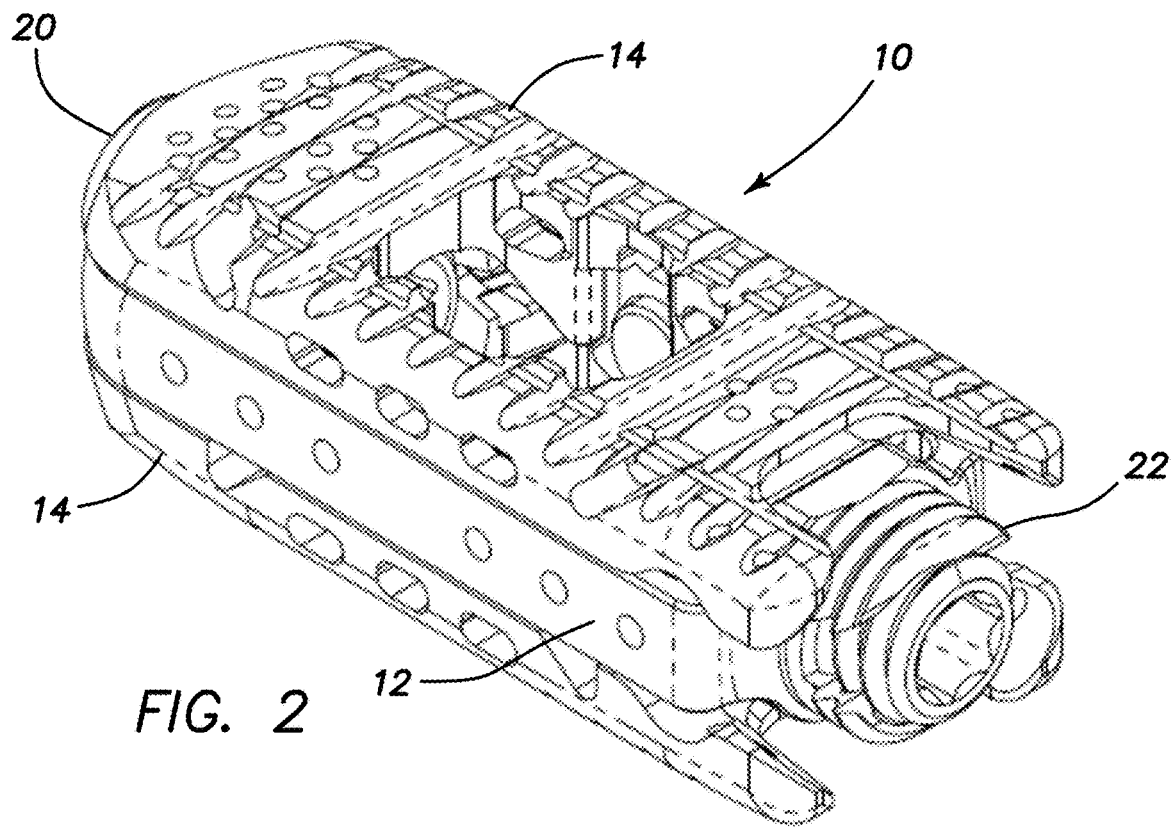
FIG. 2 is a rear top perspective view of the expandable interbody spacer of FIG. 1 in its low-profile configuration.
Figure 3:
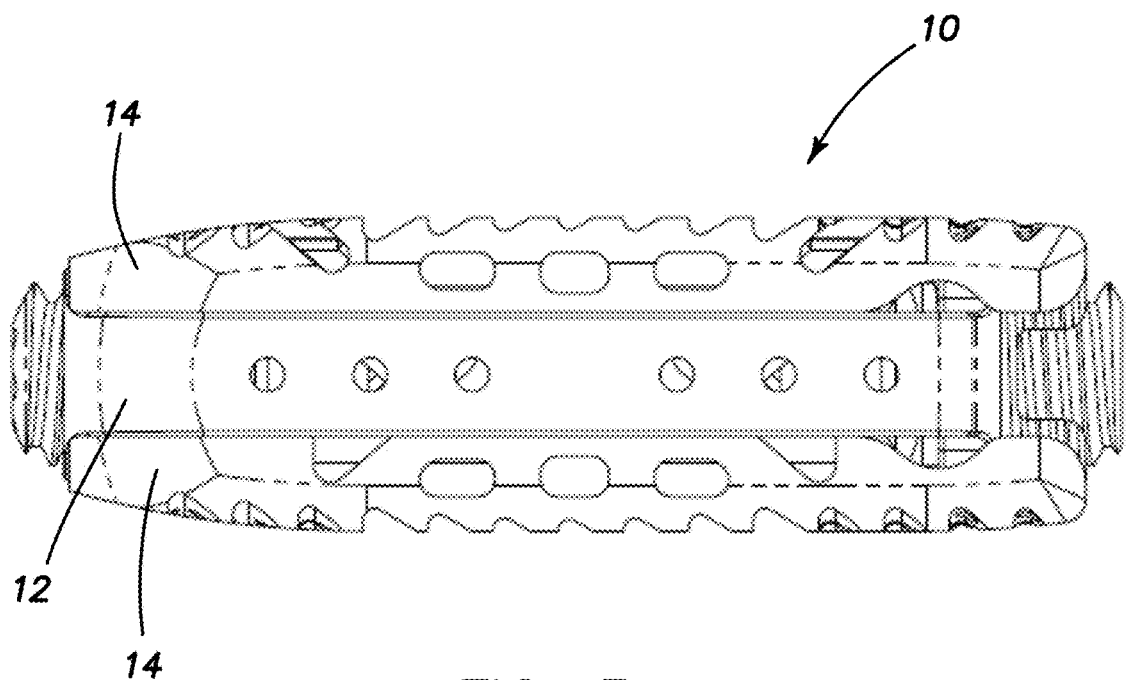
FIG. 3 is a side elevational view of the expandable interbody spacer of FIG. 1.
Figure 4:
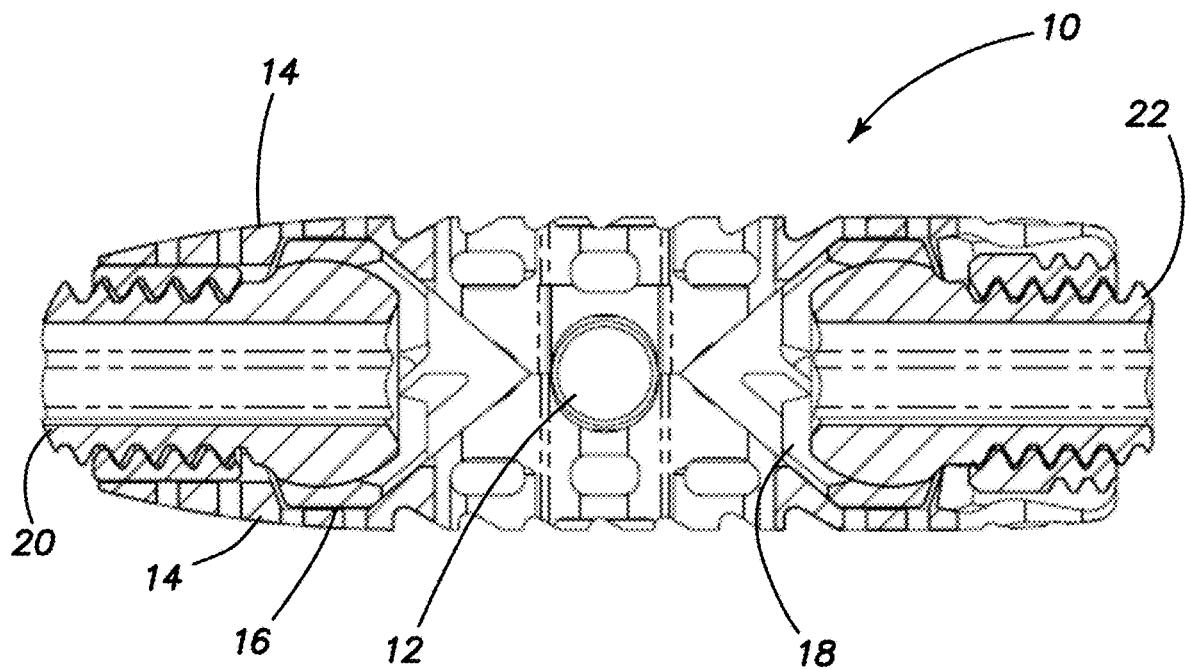
FIG. 4 is a cross-sectional view of the expandable interbody spacer of FIG. 1.

An expandable interbody spacer that is movable from an unexpanded configuration into a variety of expanded configurations including uniform parallel expansion, anterior angulation, posterior angulation and a combination of parallel expansion and anterior or posterior angulation is described below. FIGS. 1-4 depict an expandable interbody spacer 10 in an unexpanded configuration. The spacer 10 is typically used to stabilize or fuse vertebral bodies in the lumbar or other region of the spine. With particular reference to the exploded view of FIG. 5, the expandable interbody spacer 10 includes a housing 12, upper and lower endplates 14, an anterior actuator 16, a posterior actuator 18, an anterior drive screw 20, and a posterior drive screw 22. The expandable interbody spacer 10 is insertable into the disc space between two adjacent vertebral bodies from a posterior approach while in an unexpanded state illustrated in FIGS. 1-4. Generally, the unexpanded state is characterized by a low-profile configuration in which the height of the spacer 10 is the lowest and the endplates 14 are parallel to each other. Once inserted and properly positioned inside the disc space, both upper and lower endplates 14 are expanded in height on both sides of the housing 12 into an expanded state. The spacer 10 has a number of possible expanded states. The expanded states include parallel expansion, angular expansion, or a combination of both angular and parallel expansion and, furthermore, the spacer 10 has two types of angular expansion—anterior angular expansion and posterior angular expansion. In the expanded state characterized by parallel expansion, the endplates 14 are moved away from the housing 12 to increase the distance between the endplates 14 in a uniform manner such that the endplates 14 remain parallel to each other in the expanded state. In anterior angular expansion, the height of the spacer 10 at the anterior end, also called the distal end, is greater than the height of the spacer 10 at the posterior end, also called the proximal end. In posterior angular expansion, the height of the spacer 10 at the posterior end is greater than the height of the spacer 10 at the anterior end. The expanded states are effected by a unique driver 23 that selectively engages with the anterior drive screw 20, posterior drive screw 22 or both. As one or both of the anterior drive screw 20 and posterior drive screw 22 are engaged by the driver 23 and rotated, the anterior actuator 16, posterior actuator 18 or both are moved to wedge the endplates 14 into one of the expanded states.

Figure 6:
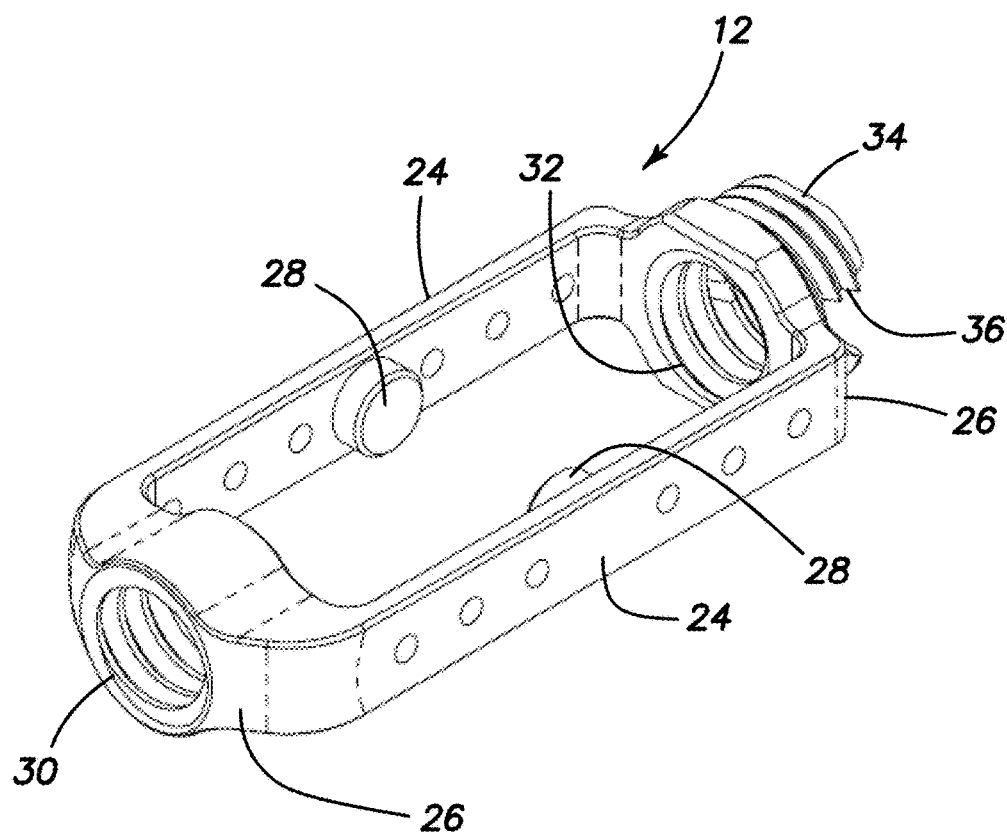
FIG. 6 is a top perspective view of a housing of the expandable interbody spacer according to the present invention.
Figure 7:
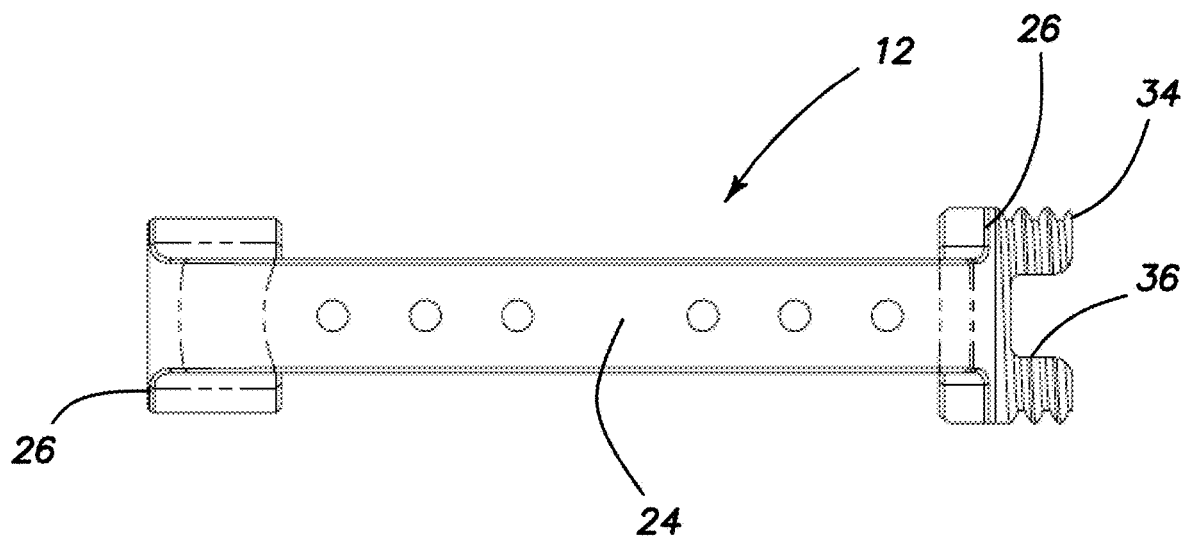
FIG. 7 is a side elevational view of the housing of FIG. 6.
Figure 8:
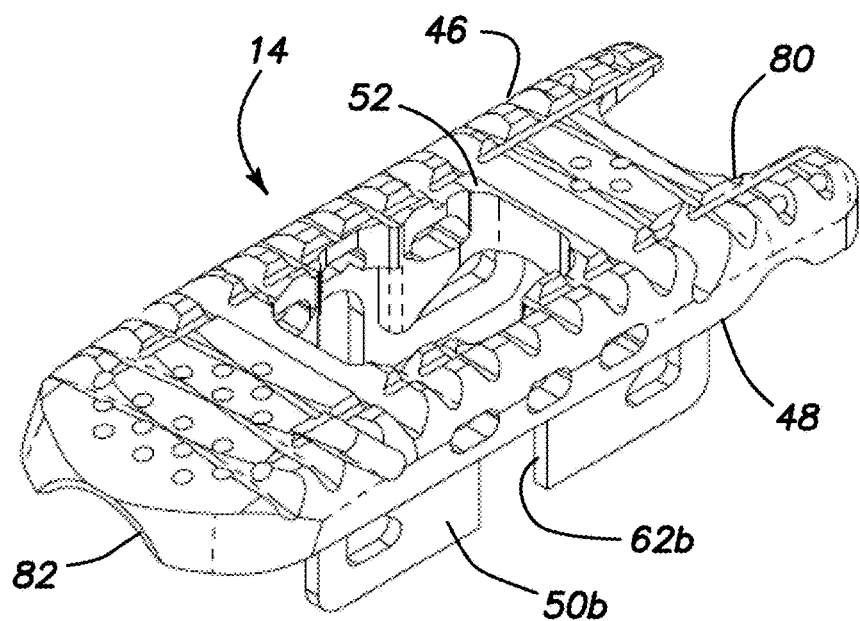
FIG. 8 is a top perspective view of an endplate of the expandable interbody spacer according to the present invention.
Figure 9A:
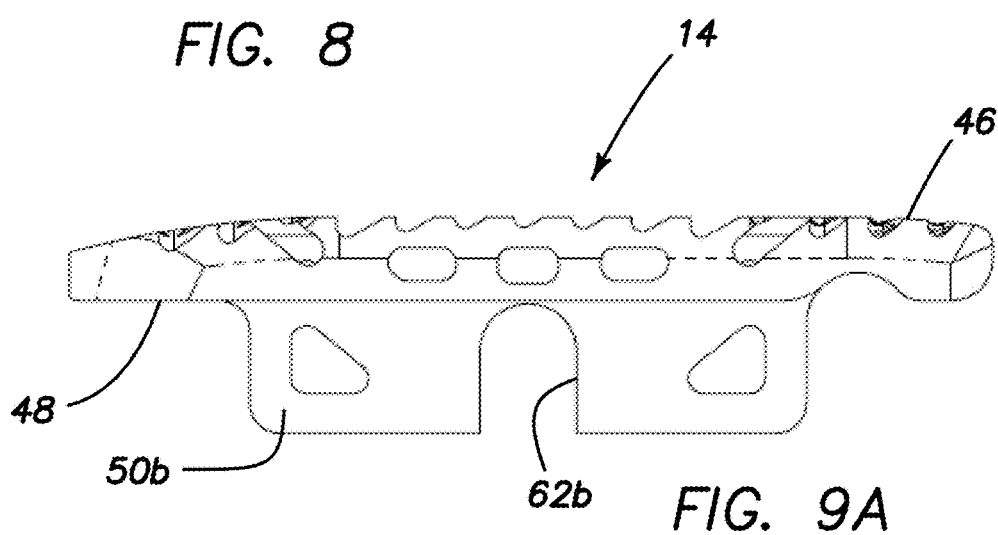
FIG. 9A is a side elevational view of the endplate of FIG. 8.
Figure 9B:
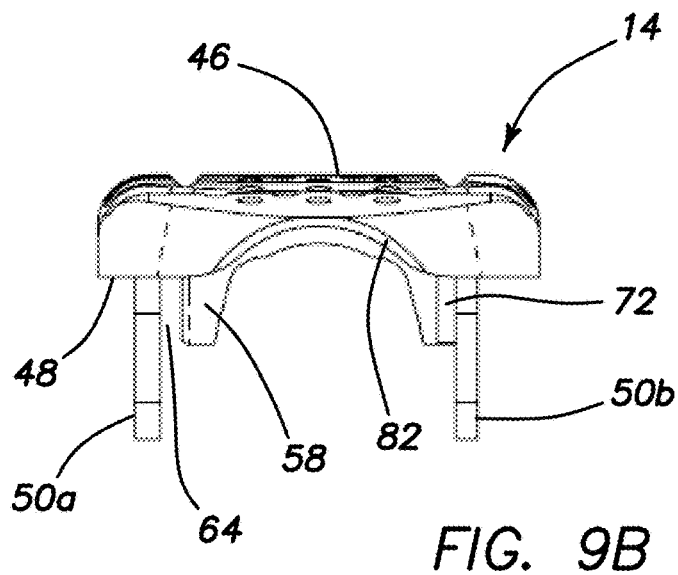
FIG. 9B is a front elevational end view of the endplate of FIG. 8.

Turning now to the FIGS. 6-7, the housing 12 will now be described in greater detail. The housing 12 includes two opposite sidewalls 24 interconnected by two opposite endwalls 26 that together define an open interior of the housing 12. A guidepost 28 is formed on the inner surface of each of the sidewalls 24 and opposite from each other at approximately the midpoint. The guideposts 28 are sized and configured to be engaged with vertical slots 62 formed on the upper and lower endplates 14 to align and guide the endplates 14 with respect to the housing 12. The sidewalls 24 are parallel to each other and of equal length. The endwalls 26 are parallel to each other and approximately of equal length. Both the sidewalls and endwalls 26 define a rectangular shaped housing 12 having a top end and bottom end that open to the interior. The top end and the bottom end are parallel to each other and the sidewalls 24 have a constant height. The front distal endwall 26 is slightly curved and defines a threaded distal opening 30 that is sized and configured to threadingly engage with the anterior drive screw 20. The height of the housing 12 is slightly greater in the location of the distal threaded opening 30. The rear proximal endwall 26 includes a cylindrical-like collar 34 extending proximally and defining a threaded rear opening 32 that opens to the interior of the housing 12. The threaded rear opening 32 is sized and configured to threadingly engage with the posterior drive screw 22. The collar 34 includes external threads for connecting with a driver instrument 23 and notches 36 for aligning the connection with the driver 23. The height of the housing 12 is greater in the location of the proximal threaded opening 32. The top and bottom of the proximal endwall 26 includes top and bottom flats to give the collar 34 a low-profile height.

Figure 5:
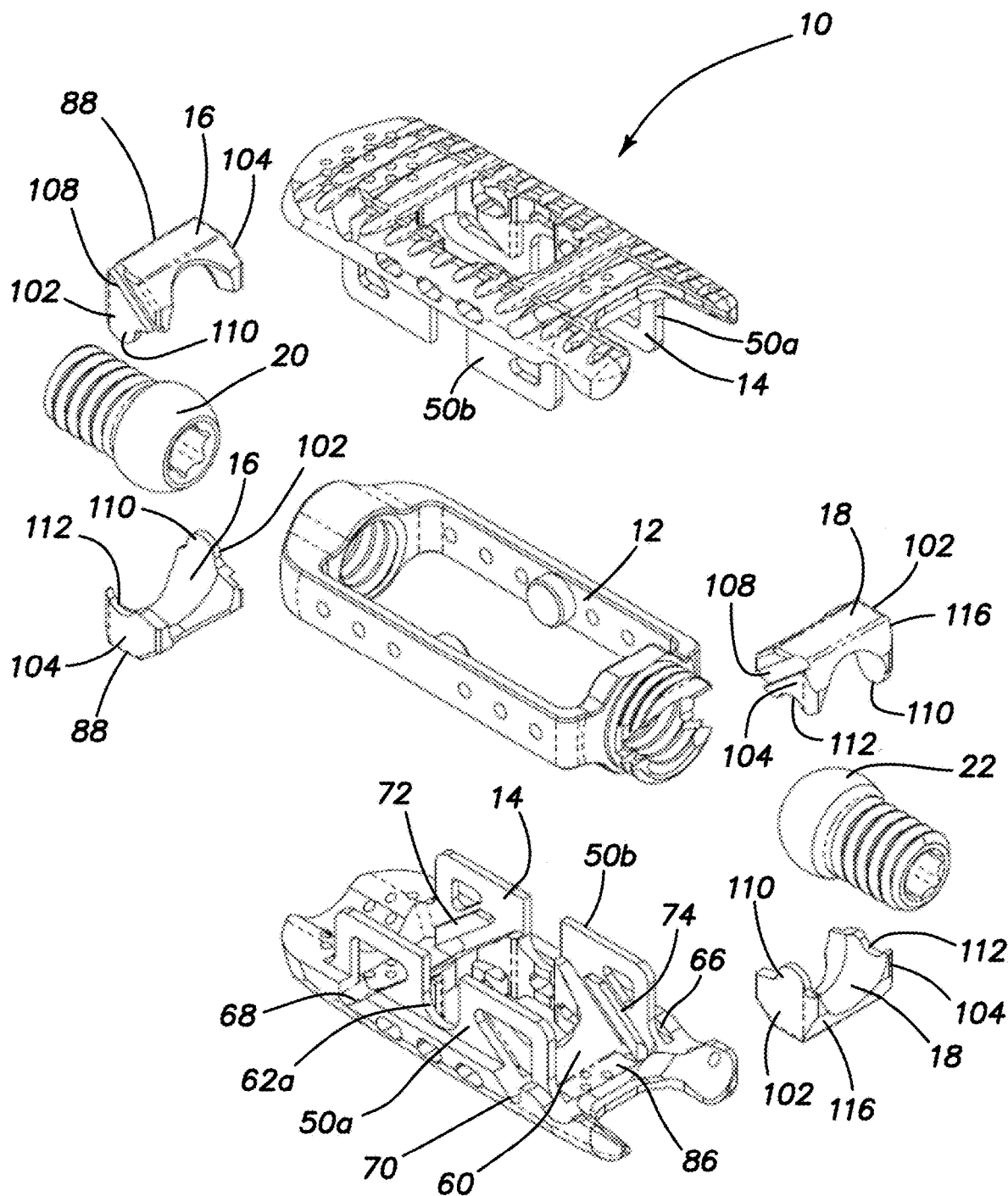
FIG. 5 is an exploded view of the expandable interbody spacer of FIG. 1.
Figure 10:
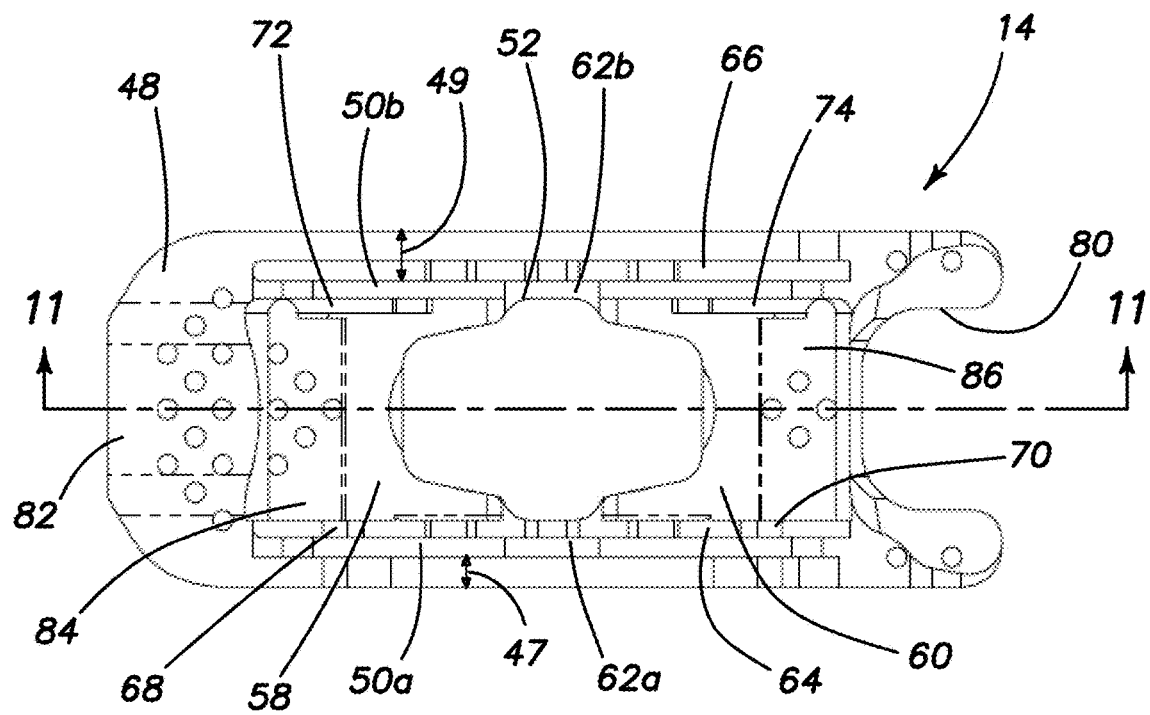
FIG. 10 is a bottom view of the endplate of FIG. 8.
Figure 11:
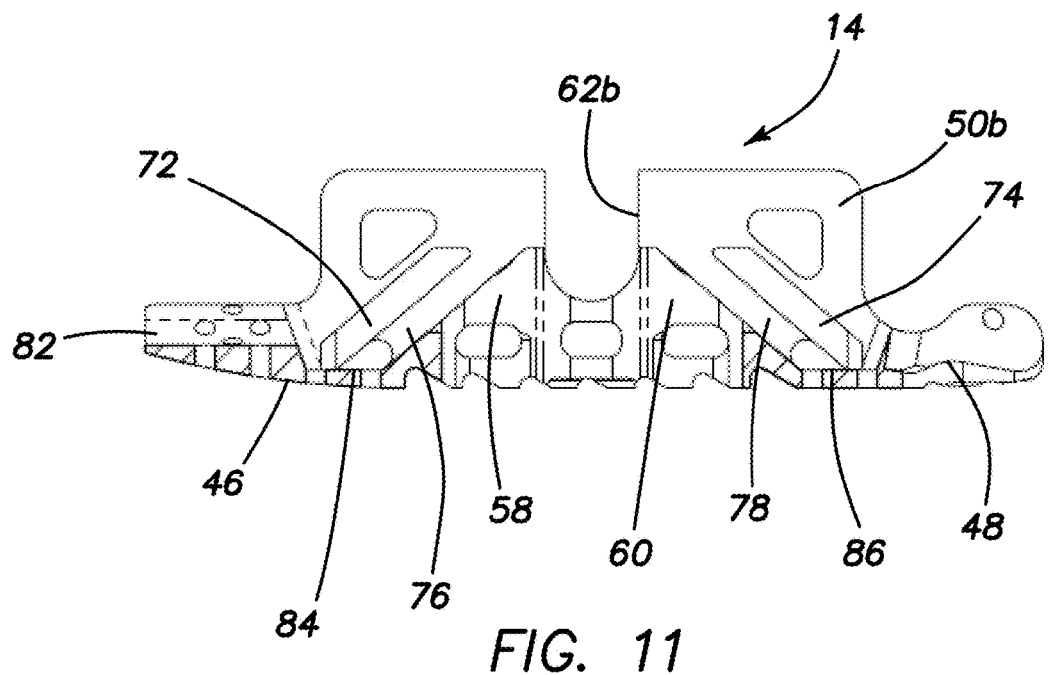
FIG. 11 is a cross-sectional view of the endplate taken along line 11-11 of FIG. 10.

Turning to FIGS. 8-11, the upper and lower endplates 14 will now be described. The upper and lower endplates 14 are identical and are connected to the housing 12 via the anterior and posterior actuators 16, 18 and the anterior and posterior drive screws 20, 22 threaded into the housing 12. Each endplate 14 has a bone-engaging surface 46 and an interior surface 48 opposite from the bone-engaging surface 46. The bone-engaging surface 46 includes a plurality of tooth-like ridges. The ridges have pointed peaks to engage and increase the purchase on the adjacent vertebra between which the spacer 12 is located. The ridges may further be angled to help hold and directionally prevent migration of the spacer 10 relative to the adjacent vertebrae when implanted within the intervertebral space. The endplate 14 further includes a leading surface 55 that does not have tooth-like projections. The leading surface 55 is slightly angled to form a leading ramp-like surface at the distal end for easier penetration and distraction of the disc space as the spacer 10 is inserted. Each endplate 14 includes at least one endplate opening 52 extending between the bone-engaging surface 46 and the interior surface 48 and opening to the interior of the housing 12. The endplate opening 52 reduces the weight of the spacer 10 and permits bone ingrowth to take place into the endplate 14. A family of bone graft materials, such as autograft, bone morphogenic protein (BMP), bone marrow aspirate, concentrate, stem cells and the like, may be placed inside the endplate openings 52 and into the interior of the housing 12 to promote bone growth into the spacer 10. Also, small holes may be formed in the bone-engaging surface 46 to promote osseointegration. The bone-engaging surface 46 of the endplates 14 are substantially flat and parallel to each other when in the collapsed, low-profile unexpanded state. The endplates 14 have a width that is approximately equal to the overall width of the spacer 10 and approximately equal to the width of the housing 12. Each endplate 14 includes two oppositely-disposed and parallel side rails, a first side rail 50a and a second side rail 50b, extending perpendicularly from the interior surface 48. The first side rail 50a includes an inner surface facing the longitudinal axis of the endplate 14 and an outer surface facing outwardly. The first side rail 50a is offset inwardly from the adjacent side edge of the bone-engaging surface 46 by a first distance 47. The first side rail 50a includes a U-shaped slot 62a that is perpendicular to the horizontal plane. The slot 62a is sized and configured to receive a guidepost 28 of the housing 12. The second side rail 50b includes an inner surface facing the longitudinal axis of the endplate 14 and an outer surface facing outwardly. The second side rail 50b is offset inwardly from the adjacent side edge by a second distance 49 wherein the second distance 49 is greater than the first distance 47. The second side rail 50b includes a U-shaped slot 62b that is perpendicular to the horizontal plane. The slot 62b is sized and configured to receive a guidepost 28 of the housing 12. The slots 62a, 62b are oppositely disposed and aligned with each other. The endplate 14 further includes an anterior ramp 58 and a posterior ramp 60. The anterior ramp 58 is located proximal to the anterior end of the endplate 14. The anterior ramp 58 extends at an angle from the interior surface 48 of the endplate 14. The angle of the anterior ramp 58 is such that the height of the anterior ramp 58 increases toward the posterior end of the endplate 14 as clearly shown in FIG. 11. The anterior ramp 58 is U-like in shape with the opening of U-shape facing the center of the endplate 14. The posterior ramp 60 is located proximal to the posterior end of the endplate 14. The angle of the posterior ramp 60 is such that the height of the posterior ramp 60 increases toward the anterior end of the endplate 14 as clearly shown in FIGS. 5 and 11. The posterior ramp 60 is also U-like in shape with the opening of the U-shape facing the center of the endplate 14. The top ends of the U-shaped ramps 58, 60 meet and are aligned with the slots 62a, 62b. A first gap or channel 64 is defined and formed between the first side rail 50a and the anterior and posterior ramps 58, 60 as can be seen in FIGS. 9B and 10. The first channel 64 is sized and configured to receive the second side rail 50b of the lower endplate 14. As previously mentioned, the upper and lower endplates 14 are identical. Due to the offset distances 47, 49 of the side rails 50a, 50b, the second side rail 50b of the lower endplate 14 will be received inside the first channel 64 adjacent to the inner surface of the first rail 50a of the upper endplate 14 to interlock the upper and lower endplates 14. A second gap or channel 66 is defined and formed between the second side rail 50b and the adjacent side edge of the endplate 14. The second channel 66 can be seen in FIG. 10. The second channel 66 is located within the second distance 49. The second channel 66 is sized and configured to receive first side rail 50a of the lower endplate 14. Due to the offset distances 47, 49 of the side rails 50a, 50b, the first side rail 50a of the lower endplate 14 will be received inside the second channel 66 adjacent to the outer surface of the second rail 50b of the upper endplate 14 to interlock the upper and lower endplates 14. With particular reference to FIGS. 5 and 10, the first and second channels 64, 66 are grooves formed into the interior surface 48 of the endplate 14 and are slightly longer in length than the length of the side rails 50a, 50b in order to accommodate the siderails 50a, 50b during angulation. Formed within the first channel 64 is an anterior indent 68 and a posterior indent 70 sized and configured to receive a portion of the anterior and posterior actuators 16, 18, respectively. There is no gap or channel between the anterior and posterior ramps 58, 60 and the second side rail 50b. The inner surface of the second side rail 50b includes an anterior projection 72 and a posterior projection 74 shown in FIGS. 5, 9B, 10 and 11. The anterior projection 72 extends outwardly from the inner surface of the second side rail 50b toward the longitudinal axis of the endplate 14. The anterior projection 72 is angled parallel to the angle of the anterior ramp 58. The anterior projection 72 is spaced apart from the anterior ramp 58 surface defining an anterior recess 76 therebetween. The anterior recess 76 is sized and configured to receive and guide part of the anterior actuator 16 which will be described in greater detail below. The posterior projection 74 extends outwardly from the inner surface of the second side rail 50b toward the longitudinal axis of the endplate 14. The posterior projection 74 is angled parallel to the angle of the posterior ramp 58. The posterior projection 74 is spaced apart from the posterior ramp 60 surface defining a posterior recess 78 therebetween. The posterior recess 78 is sized and configured to receive and guide part of the posterior actuator 18 which will be described in greater detail below. The interior surface 48 of the endplate 14 includes a concave area 82 that corresponds to and accommodates the convex surface of the distal endwall 26 of the housing 12 in the location of the distal threaded opening 30. The concave area 82 provides the spacer 10 with a low-profile configuration while allowing for a larger anterior drive screw to be utilized. The posterior end of the endplate 14 includes a cutout 80 that is sized and configured to clear the proximal collar 34 of the housing 12 during angulation of the anterior end and to provide the spacer 10 with the lowest profile, largest bone-engaging surface 46, largest posterior drive screw 22 for strength and a greater range of angulation. With particular reference to FIGS. 5, 10 and 11, the endplate 14 further includes a rectangular-shaped anterior well 84 that is sized and configured to receive part of the anterior actuator 16 when the spacer 10 is in the unexpanded state. The endplate 14 also includes a rectangular-shaped posterior well 86 that is sized and configured to receive part of the posterior actuator 18 when the spacer 10 is in the unexpanded state. The wells 84, 86 are depressions formed into the interior surface 48 of the endplate 14 that permits the actuators 16, 18 a larger range of translation providing a lower profile in the unexpanded state compared to the absence of such wells 84, 86.

Turning now to FIGS. 12A-12H, the anterior actuator 16 will now be described in greater detail. The anterior actuator 16 comprises of two identical anterior actuator segments 88 wherein one anterior actuator segment 88 is inverted with respect to the other anterior actuator segment 88 and mated therewith. With reference back to FIG. 5, an upper anterior actuator segment 88 is adjacent to the upper endplate 14 and a lower anterior actuator segment 88 is adjacent to the lower endplate 14. The upper anterior actuator segment 88 together with the lower anterior actuator segment 88 form the anterior actuator 16.

With continued reference to FIGS. 12A-12H, the anterior actuator segment 88 includes a leading surface 90, a trailing surface 92, a landing surface 94, a front wall 96, a rear wall 98, and an inner surface 100 all integrally interconnected by a first sidewall 102 and a second sidewall 104. The leading surface 90 includes a scallop 106 sized and configured to accommodate part of the anterior drive screw 20. The scallop 106 corresponds to the U-shaped anterior ramp 58 and defines a contact area of the leading surface 90 that corresponds substantially to the contact area of the anterior ramp 58. The leading surface 90 is angled. The angle of the leading surface 90 corresponds to the angle of the anterior ramp 58 such that ideal mating contact is maintained during expansion of the spacer 10 for a uniform distribution of forces when loaded in situ. The angled leading surface 90 is sized and configured to contact the anterior ramp 58 of the endplate 14 and slide along the anterior ramp 58 to move the endplate 14 into expansion or reduction as the anterior drive screw 20 is threadingly translated. The trailing surface 92 is angled toward the vertical rear wall 98 to provide a tapered actuator segment 88. The landing surface 94 is substantially rectangular in shape and includes a notch in the location of the side channel 108. The landing surface 94 is flat, horizontally orientated and sized and configured to fit inside the anterior well 84 of the endplate 14. The front wall 96 is vertical and substantially parallel to the rear wall 98. The first sidewall 102 and second sidewall 104 are parallel to each other and vertical in orientation. The first sidewall 102 includes a side channel 108 having an angle equal to the angle of the leading surface 90. The side channel 108 is sized and configured to receive the anterior projection 72 of the endplate 14 within the side channel 108. The anterior projection 72 when mated with the side channel 108 serves to hold the endplates 14 and anterior actuator 16 together and in position and also serves to guide the movement of the anterior actuator 16 along the anterior ramp 58. The first sidewall 102 includes a curved projection 110 that is sized and configured to mate with a curved indentation 112 on the second sidewall 104 of an adjacent and up-side down-oriented anterior actuator segment 88 comprising the anterior actuator 16. The inner surface 100 is curved to match the curvature of the ball head of the anterior drive screw 20. The inner surface 100 is spherical in shape and, in particular, it is semi-spherical in shape and further it is truncated and semi-spherical in shape.

Figure 12A:
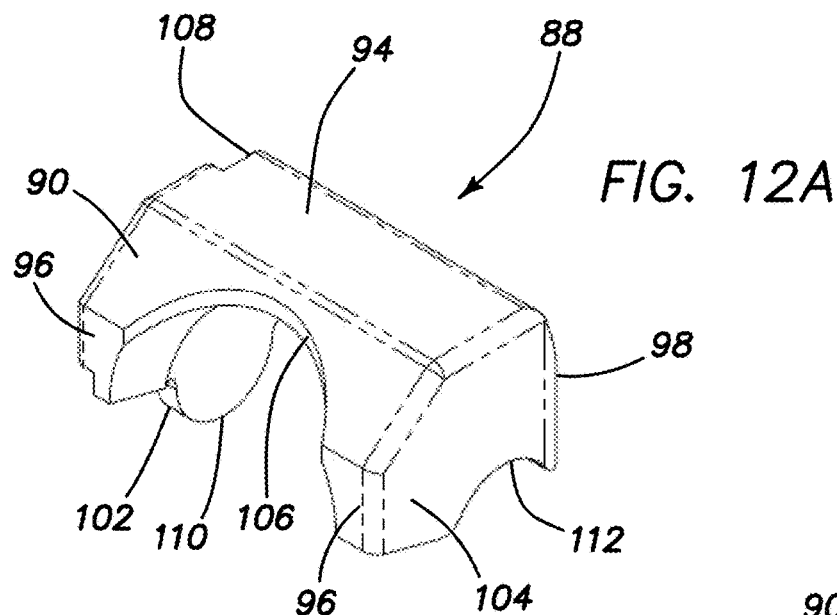
FIG. 12A is a top perspective view of an anterior actuator segment of the expandable interbody spacer of FIG. 1.
Figure 12B:
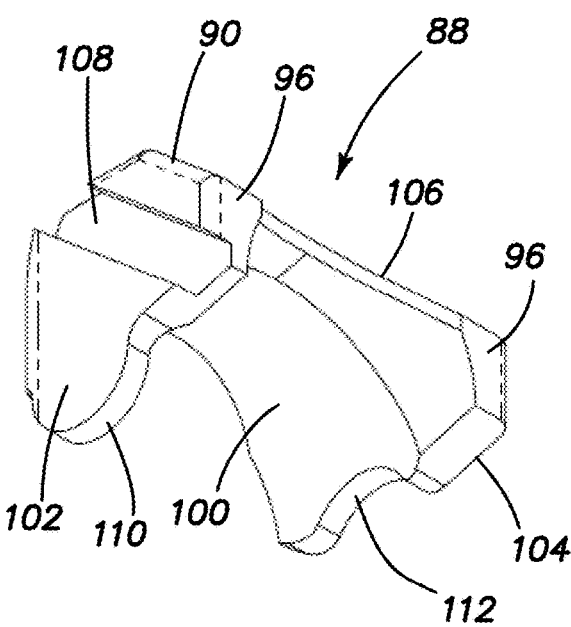
FIG. 12B is a bottom perspective view of the anterior actuator segment of FIG. 12A.
Figure 12C:
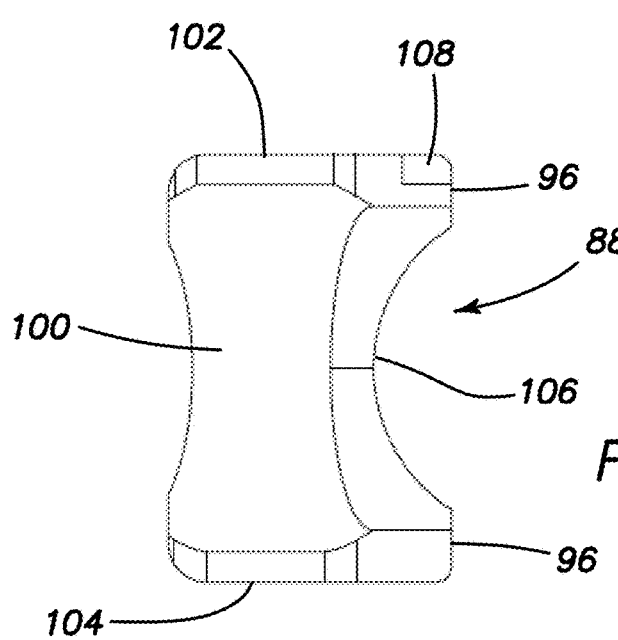
FIG. 12C is a bottom view of the anterior actuator segment of FIG. 12A.
Figure 12D:
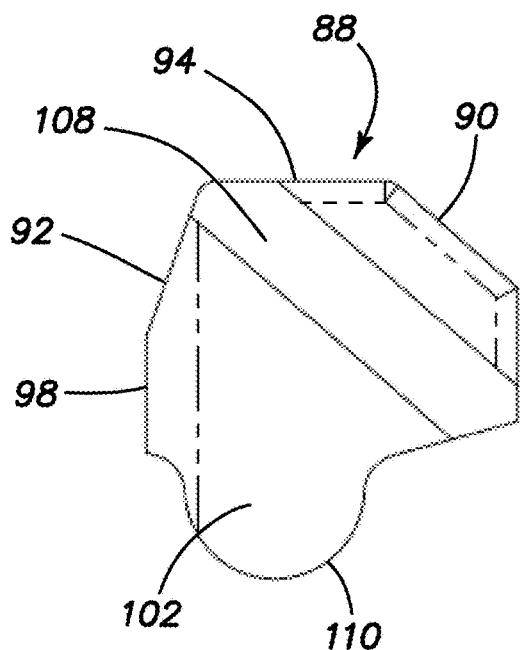
FIG. 12D is a side view of the anterior actuator segment of FIG. 12A.
Figure 12E:
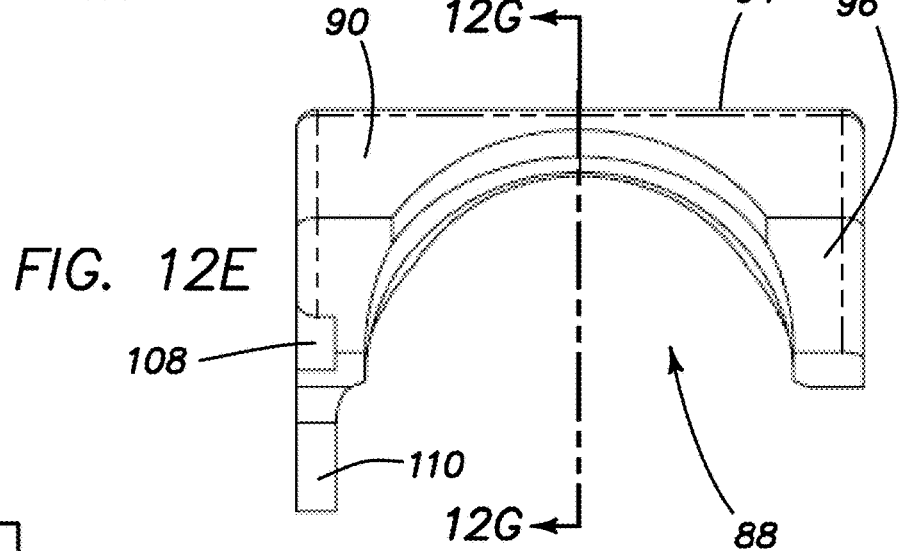
FIG. 12E is an end view of the anterior actuator segment of FIG. 12A.
Figure 12F:
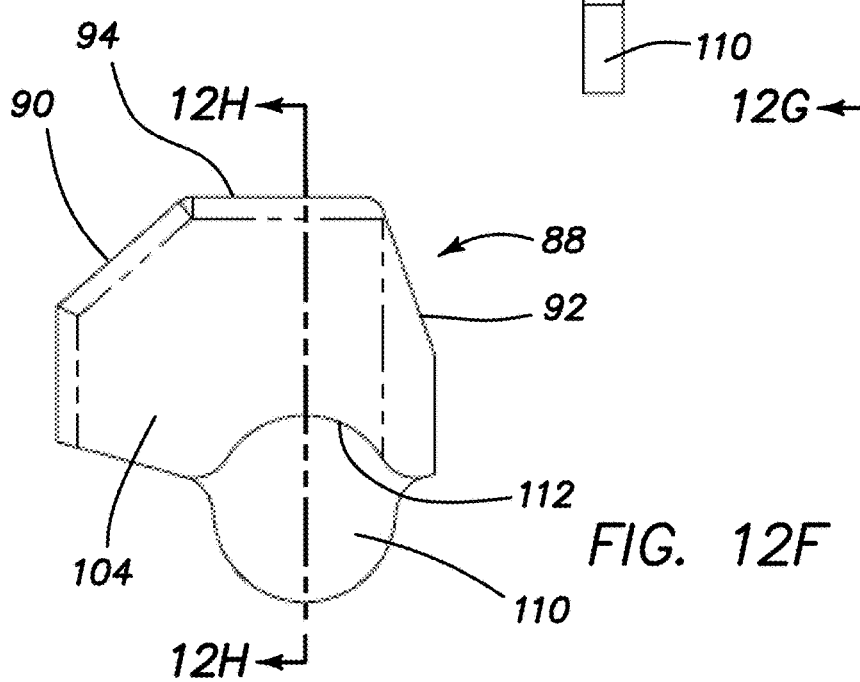
FIG. 12F is a side view of the anterior actuator segment of FIG. 12A.
Figure 12G:
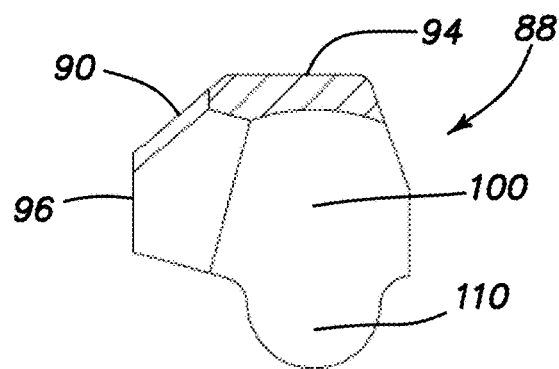
FIG. 12G is a cross-sectional view of the anterior actuator segment taken along line 12G-12G of FIG. 12E.
Figure 12H:
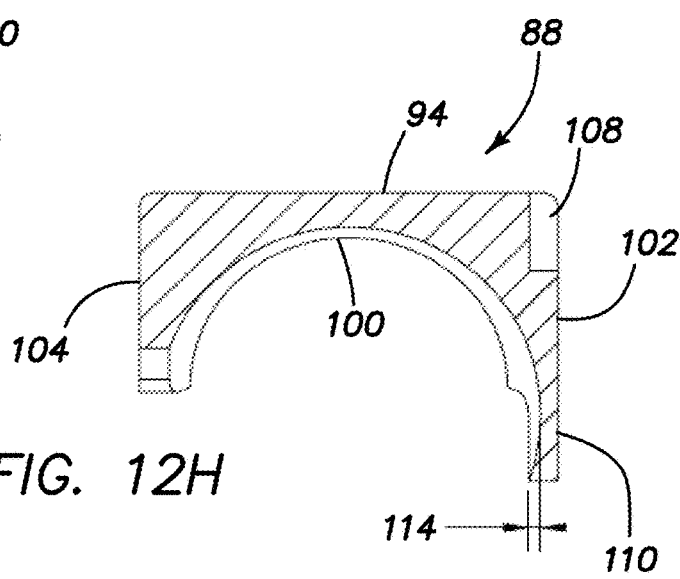
FIG. 12H is a cross-sectional view of the anterior actuator segment taken along line 12H-12H of FIG. 12F.

As mentioned previously, the upper anterior actuator segment 88 is identical to the lower anterior actuator segment 88 and that together they are joined to form the anterior actuator 16. One of the two identical anterior actuator segments 88 of the anterior actuator 16 is turned upside down or inverted such that the inner surfaces 100 face each other. The lower anterior actuator segment 88 is adjacent to the lower endplate 14 and the upper anterior actuator segment 88 is adjacent to the upper endplate 14. As can be seen in FIG. 5, the first sidewall 102 of the lower anterior actuator segment 88 faces the second side rail 50b of the lower endplate 14 and, as such, the side channel 108 of the lower actuator segment 88 engages with the anterior projection 72 of the lower endplate 14 whereas the first sidewall 102 of the upper anterior actuator segment 88 is on the opposite side and faces the second side rail 50b of the upper endplate 14 and, as such, the side channel 108 of the upper actuator segment 88 engages with the anterior projection 72 of the upper endplate 14. The curved projection 110 of the upper anterior actuator segment 88 mates with the curved indentation 112 of the lower anterior actuator segment 88 on one side and the curved projection 110 of the lower anterior actuator segment 88 mates with the curved indentation 112 of the upper anterior actuator segment 88. The mated upper and lower anterior actuator segments 88 form a clamshell-like chamber that captures the anterior drive screw 20. The ball head 118 of the anterior drive screw 20 is located between the upper anterior actuator segment 88 and the lower anterior actuator segment 88 and captured inside the clamshell-like enclosure such that the curved, spherical ball head 118 of the anterior drive screw 20 may make contact with the truncated spherical ball shape chamber comprised of the inner surfaces 100 of the adjacent upper and lower anterior actuator segments 88 as needed for the transmission of load from the endplates 14 to the actuator 16 to the drive screw 20 and, in turn, to the housing 12 while permitting the drive screw 20 to rotate about its axis relative to the anterior actuator 16. The leading surfaces 90 of the upper and lower anterior actuator segments 88 face toward the proximal end and are angled such that the distance between the leading surfaces 90 increases towards the distal end. With particular reference to FIG. 12H, the first sidewall 102 depends downwardly or otherwise extends in the location of the curved projection 110 such that the curvature of the spherical inner surface 100 is longer than a semi-circle to define an overhang 114 wherein the slope of a plane tangential to the cross-sectional curve goes from a negative value to a positive value in the location of the curved projection 110. This overhang 114 advantageously causes the ball head 118 of the drive screw 20 to snap in position past the overhangs 114 of both anterior actuator segments 88 and to be held in place by the overhangs 114.

Turning now to FIGS. 13A-13H, the posterior actuator 18 will now be described in greater detail wherein like numbers are used to describe like parts. The posterior actuator 18 is comprised of two identical posterior actuator segments 116 wherein one posterior actuator segment 116 is inverted with respect to the other posterior actuator segment 116 and mated therewith. With reference back to FIG. 5, an upper posterior actuator segment 116 is adjacent to the upper endplate 14 and a lower anterior actuator segment 116 is adjacent to the lower endplate 14. The upper anterior actuator segment 116 together with the lower anterior actuator segment 116 form the anterior actuator 18.

With continued reference to FIGS. 13A-13H, the posterior actuator segment 116 includes a leading surface 90, a trailing surface 92, a landing surface 94, a front wall 96, a rear wall 98, and an inner surface 100 all integrally interconnected by a first sidewall 102 and a second sidewall 104. The leading surface 90 includes a scallop 106 sized and configured to accommodate part of the posterior drive screw 22. The scallop 106 corresponds to the U-shaped posterior ramp 60 and defines a contact area of the leading surface 90 that corresponds substantially to the contact area of the posterior ramp 60. The leading surface 90 is angled. The angle of the leading surface 90 corresponds to the angle of the posterior ramp 60 such that ideal mating contact is maintained during expansion of the spacer 10 for a uniform distribution of forces when loaded in situ. The angled leading surface 90 is sized and configured to contact the posterior ramp 60 of the endplate 14 and slide along the posterior ramp 60 to move the endplate 14 into expansion or reduction as the posterior drive screw 22 is threadingly translated. The trailing surface 92 is angled toward the vertical rear wall 98 to provide a tapered actuator segment 116. The landing surface 94 is substantially rectangular in shape and includes a notch in the location of the side channel 108. The landing surface 94 is flat, horizontally orientated and sized and configured to fit inside the posterior well 86 of the endplate 14. The front wall 96 is vertical and substantially parallel to the rear wall 98. The first sidewall 102 and second sidewall 104 are parallel to each other and vertical in orientation. Unlike the anterior actuator segment 88, the second sidewall 104 of the posterior actuator segment 116 includes a side channel 108 having an angle equal to the angle of the leading surface 90. The side channel 108 is sized and configured to receive the posterior projection 74 of the endplate 14 within the side channel 108 having the same angle. The posterior projection 74 when mated with the side channel 108 serves to hold the endplates 14 and posterior actuator 18 together and in position and also serves to guide the movement of the posterior actuator 18 along the posterior ramp 60. The first sidewall 102 includes a curved projection 110 that is sized and configured to mate with a curved indentation 112 on the second sidewall 104 of an adjacent and up-side down-oriented posterior actuator segment 116 comprising the posterior actuator 18. The inner surface 100 is curved to match the curvature of the ball head of the posterior drive screw 22. The inner surface 100 is spherical in shape and, in particular, it is semi-spherical in shape and further it is truncated and semi-spherical in shape.

Figure 13A:
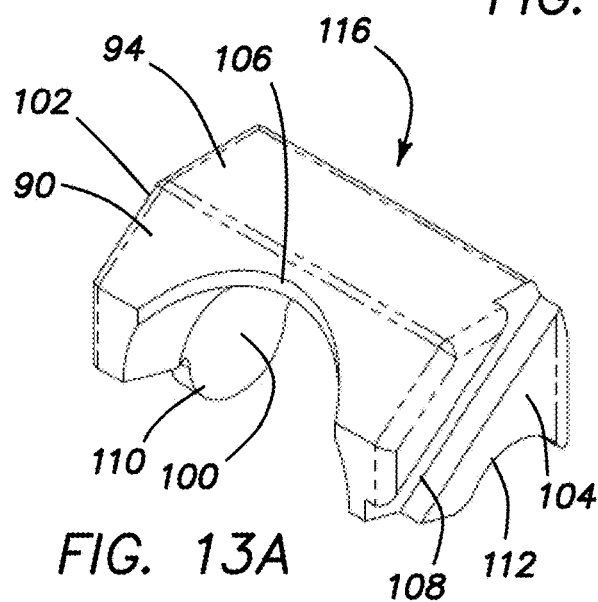
FIG. 13A is a top perspective view of a posterior actuator segment of the expandable interbody spacer of FIG. 1.
Figure 13B:
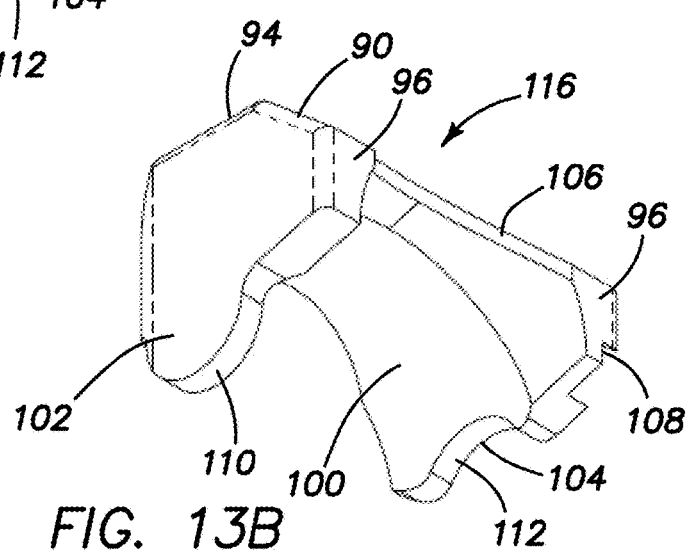
FIG. 13B is a bottom perspective view of the posterior actuator segment of FIG. 13A.
Figure 13C:
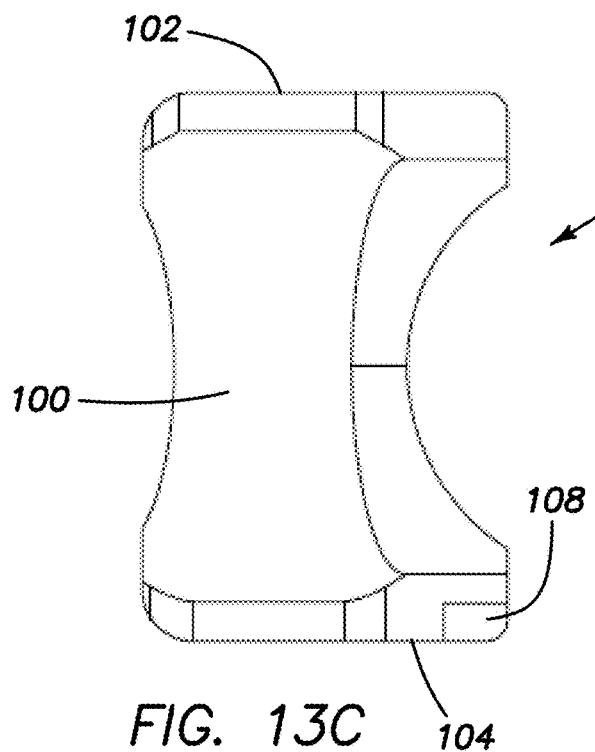
FIG. 13C is a bottom view of the posterior actuator segment of FIG. 13A.
Figure 13D:
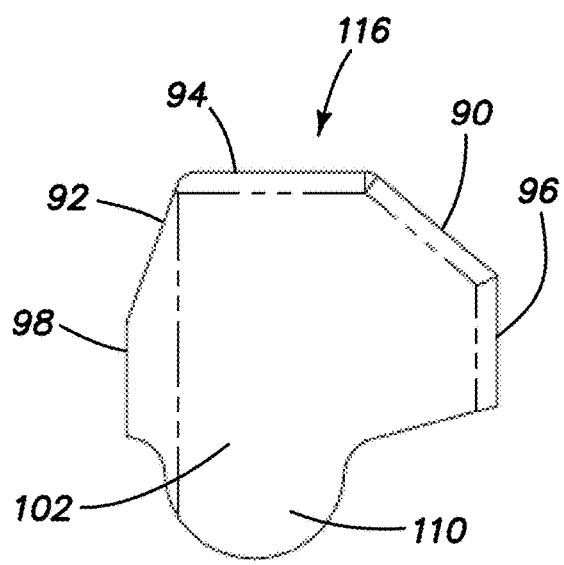
FIG. 13D is a side view of the posterior actuator segment of FIG. 13A.
Figure 13E:
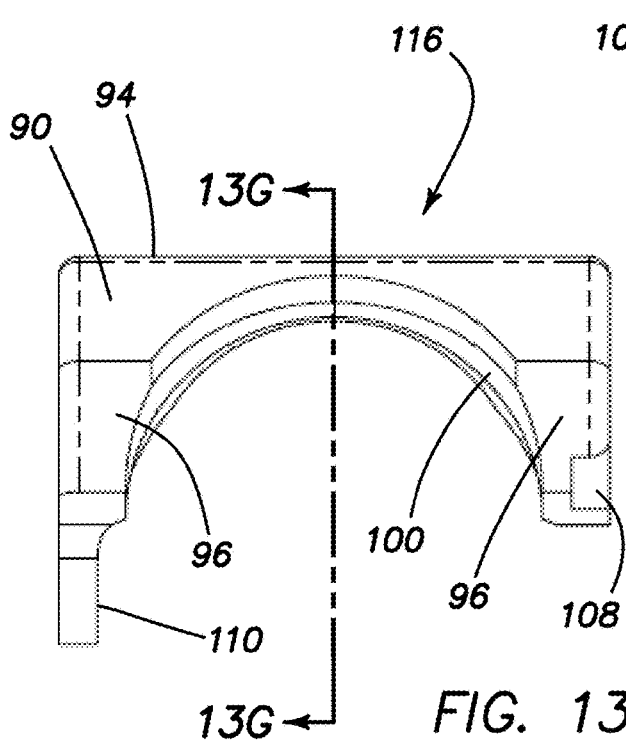
FIG. 13E is an end view of the posterior actuator segment of FIG. 13A.
Figure 13F:
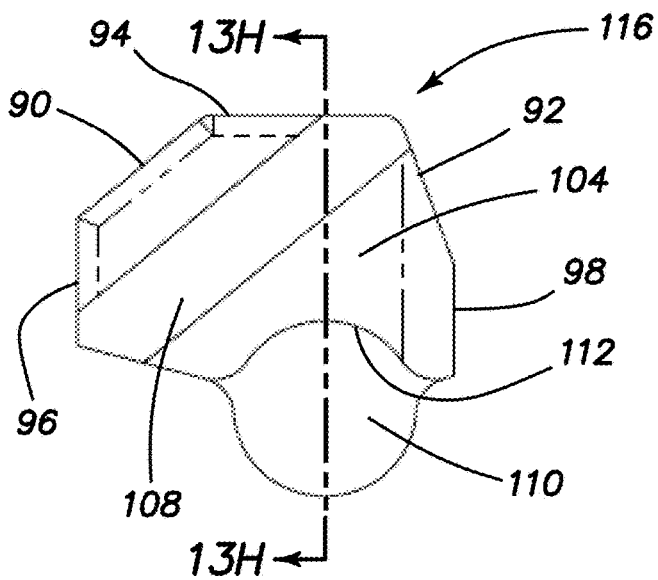
FIG. 13F is a side view of the posterior actuator segment of FIG. 13A.
Figure 13G:
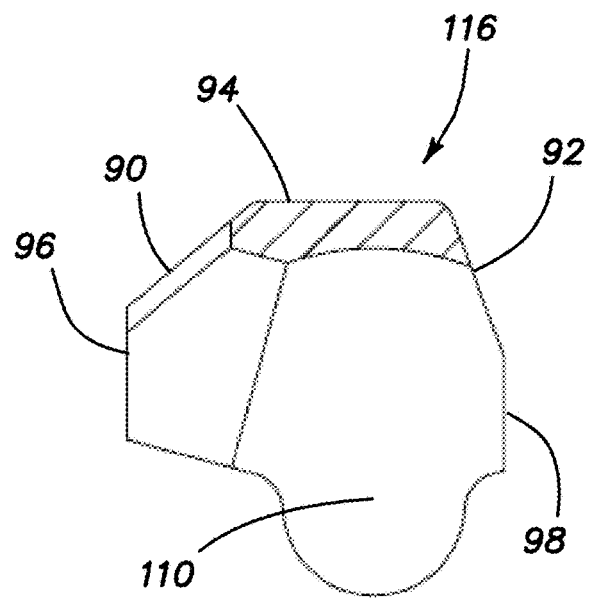
FIG. 13G is a cross-sectional view of the posterior actuator segment taken along line 13G-13G of FIG. 13E.
Figure 13H:
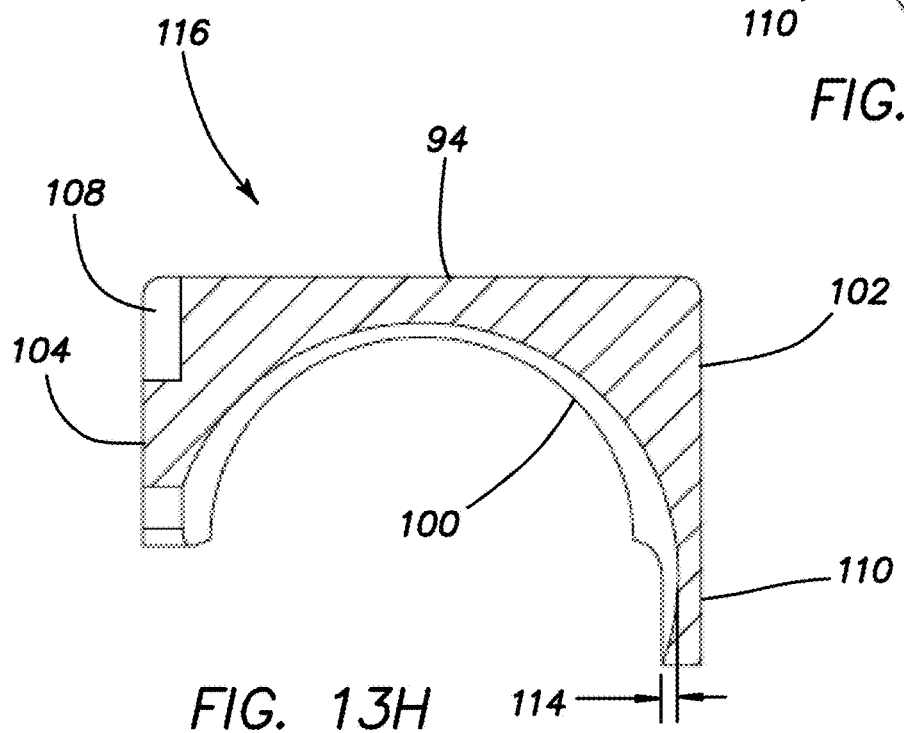
FIG. 13H is a cross-sectional view of the posterior actuator segment taken along line 13H-13H of FIG. 13F.

As mentioned previously, the upper posterior actuator segment 116 is identical to the lower posterior actuator segment 116 and that together they are joined to form the posterior actuator 18. One of the two identical posterior actuator segments 116 comprising the posterior actuator 18 is turned upside down or inverted such that the inner surfaces 100 face each other. The lower posterior actuator segment 116 is adjacent to the lower endplate 14 and the upper posterior actuator segment 116 is adjacent to the upper endplate 14. As can be seen in FIG. 5, the second sidewall 104 of the lower posterior actuator segment 116 faces the second side rail 50b of the lower endplate 14 and as such the side channel 108 of the lower actuator segment 116 is oriented to engage with the posterior projection 74 of the lower endplate 14; whereas, the second sidewall 104 of the upper posterior actuator segment 116 is on the opposite side and faces the second side rail 50b of the upper endplate 14 and as such the side channel 108 of the upper actuator segment 88 engages with the posterior projection 74 of the upper endplate 14. The curved projection 110 of the upper posterior actuator segment 116 mates with the curved indentation 112 of the lower posterior actuator segment 116 on one side and the curved projection 110 of the lower posterior actuator segment 116 mates with the curved indentation 112 of the upper posterior actuator segment 116 on the other side to form a clamshell-like chamber that captures the posterior drive screw 22 therebetween. The spherical-shaped ball head 118 of the posterior drive screw 22 is located between the upper posterior actuator segment 116 and the lower posterior actuator segment 116 and captured inside the clamshell-like enclosure such that the curved, spherical ball shape of the posterior drive screw 20 may polyaxially make contact with the truncated spherical ball shape chamber comprised of the inner surfaces 100 of the adjacent upper and lower posterior actuator segments 116 for the transmission of load from the endplates 14 to the actuator 18 to the drive screw 20 and to the housing 12 while permitting the drive screw 22 to rotate about its axis relative to posterior actuator 18. The leading surfaces 90 of the upper and lower posterior actuator segments 116 face toward the distal end and are angled such that the distance between the leading surfaces 90 increases towards the proximal end. With particular reference to FIG. 13H, the first sidewall 102 depends downwardly or otherwise extends at the curved projection 110 such that the curvature of the spherical inner surface 100 is longer than a semi-circle to define an overhang 114 wherein the slope of a plane tangential to the cross-sectional curve goes from a negative value to a positive value in the location of the curved projection 110. This overhang 114 advantageously causes the ball head 118 of the drive screw 22 to snap in position past the overhangs 114 of both posterior actuator segments 116 and to be held in place by the overhangs 114.

Figure 14A:
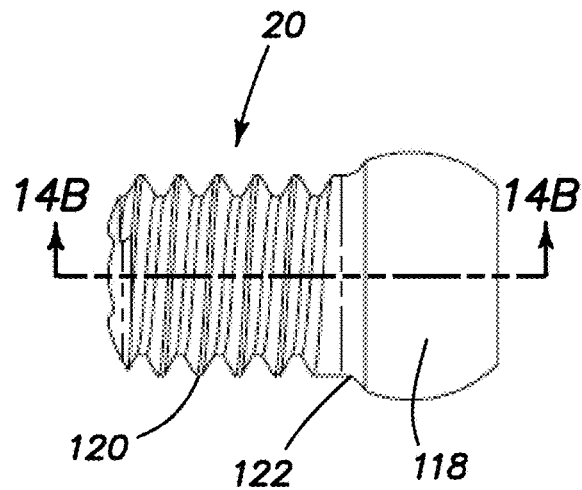
FIG. 14A is side elevational view of an anterior threaded actuator is of an expandable interbody spacer according to the present invention.
Figure 14B:
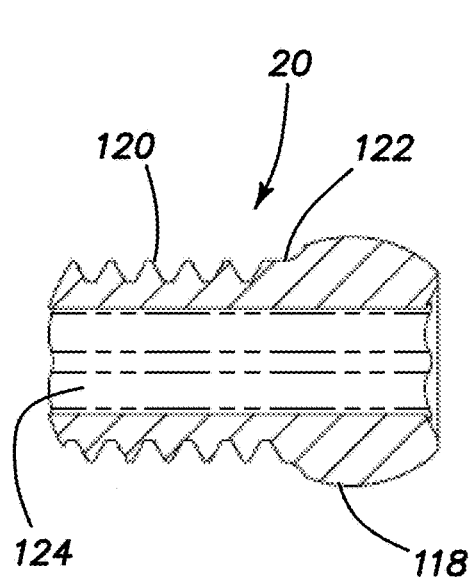
FIG. 14B is a cross-sectional view of the anterior threaded actuator taken along line 14B-14B of FIG. 14A.

Turning now to FIGS. 14A-14B, the anterior drive screw 20 will now be described. The anterior drive screw 20 includes a ball head 118 at a proximal end connected to a threaded shank portion 120 that extends toward a distal end. The ball head 118 has a spherical shape that is truncated at the shaft 120. The diameter of ball head 118 is larger than the diameter of the threaded shank 120. A neck portion 122 without threads is located between the ball head 118 and the shank 120. As can be seen in FIG. 14B, the anterior drive screw 20 includes a drive bore 124 that extends between the proximal end and the distal end of the drive screw 20. The drive bore 124 extends along the entire length of the drive screw 20 and has a proximal opening in the ball head 118 at the proximal end and a distal opening in the threaded shank 120 at the distal end. In one variation, the drive bore 124 does not have a distal opening in the threaded shank 120. The drive bore 124 has a hexalobe shape (visible in FIG. 5) or hexagonal shape in cross-section along the entire length of the bore 124. The drive bore 124 is sized and configured to be engaged to rotate the drive screw 20 by the driver instrument 23. The bore 124 may have any non-circular cross-sectional shape that is corresponds to and is sized and configured to mate with to the cross-sectional shape of distal drive portion of the driver instrument 23.

Figure 15A:
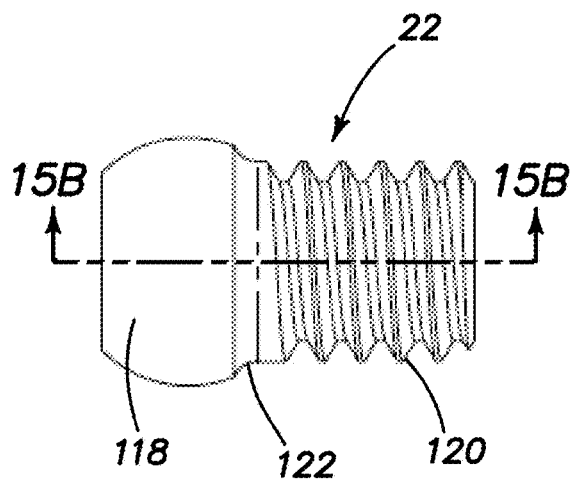
FIG. 15A is a side elevational view of a posterior threaded actuator of an expandable interbody spacer according to the present invention.
Figure 15B:
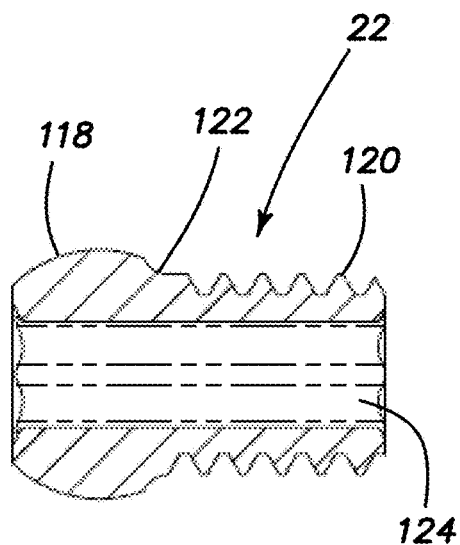
FIG. 15B is a cross-sectional view of the posterior threaded actuator taken along line 15B-15B of FIG. 15A.

Turning now to FIGS. 15A-15B, the posterior drive screw 22 will now be described wherein like reference numbers are used to describe like parts. The posterior drive screw 22 includes a ball head 118 at the distal end connected to a threaded shank portion 120 that extends toward the proximal end. The ball head 118 has a shape that is truncated at the shaft 120. The diameter of ball head 118 is larger than the diameter of the threaded shank 120. A neck portion 122 without threads is located between the ball head 118 and the shank 120. As can be seen in FIG. 15B, the posterior drive screw 22 includes a drive bore 124 that extends between the proximal end and the distal end of the drive screw 22. The drive bore 124 extends along the entire length of the drive screw 22 and has a proximal opening in the threaded shank 120 at the proximal end and a distal opening in the ball head 118 at the distal end. The drive bore 124 has a hexalobe shape (visible in FIG. 5) or hexagonal shape in cross-section along the entire length of the bore 124. The drive bore 124 is sized and configured to be matingly engaged for rotation by the driver instrument 23. The bore 124 may have any non-circular cross-sectional shape that is corresponds to and is sized and configured to mate with to the cross-sectional shape of the proximal drive portion and distal drive portion of the driver instrument 23. A non-circular cross-section will have a major diameter and minor diameter.

With reference to both FIGS. 14A-14B and FIGS. 15A-15B, the threaded shanks 120 of the anterior and posterior drive screws 20, 22 have the same length, the same size thread and the same number of threads per inch. The helical threaded shank 120 of the posterior drive screw 22 has a right-handed thread; whereas, the helical threaded shank 120 of the anterior drive screw 20 has a left-handed thread. This difference in handedness of the threads is clearly visible in FIGS. 14A and 15A. In another variation, the helical threaded shank 120 of the posterior drive screw 22 has a left-handed thread; whereas, the helical threaded shank 120 of the anterior drive screw 20 has a right-handed thread. In essence, the helical direction of one of the two drive screws 20, 22 is opposite in direction from the other. Viewing from one of the proximal end or distal end, the direction of translation with respect to the housing 12 of one of the anterior drive screw 20 and posterior drive screw 22 is positive and the direction of translation of the other one of the anterior drive screw 20 and posterior drive screw 22 is negative. The advantage of this difference will be described in greater detail below.

Figure 16:
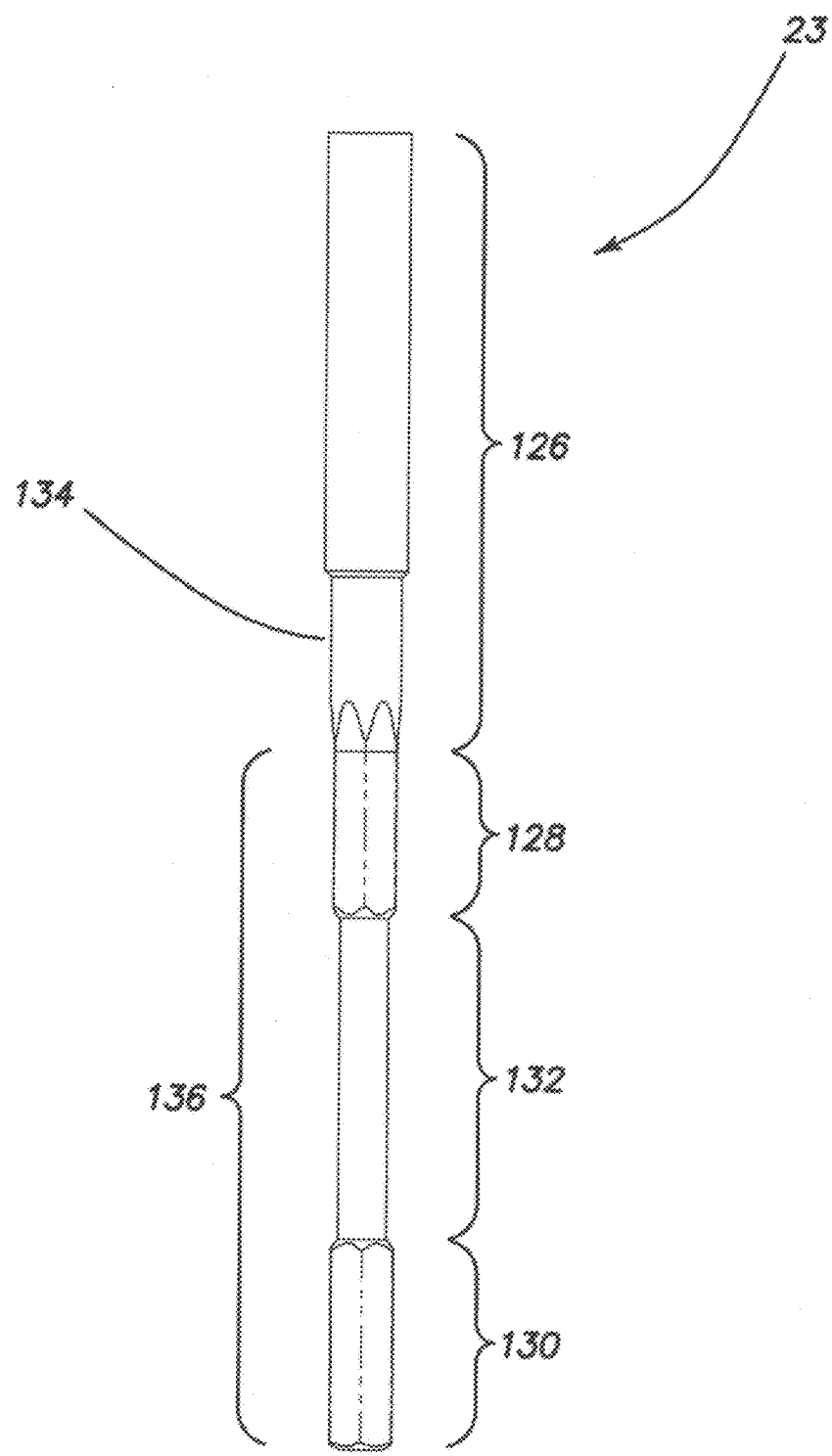
FIG. 16 is a side elevational view of a driver for the expandable interbody spacer according to the present invention.
Figure 18:
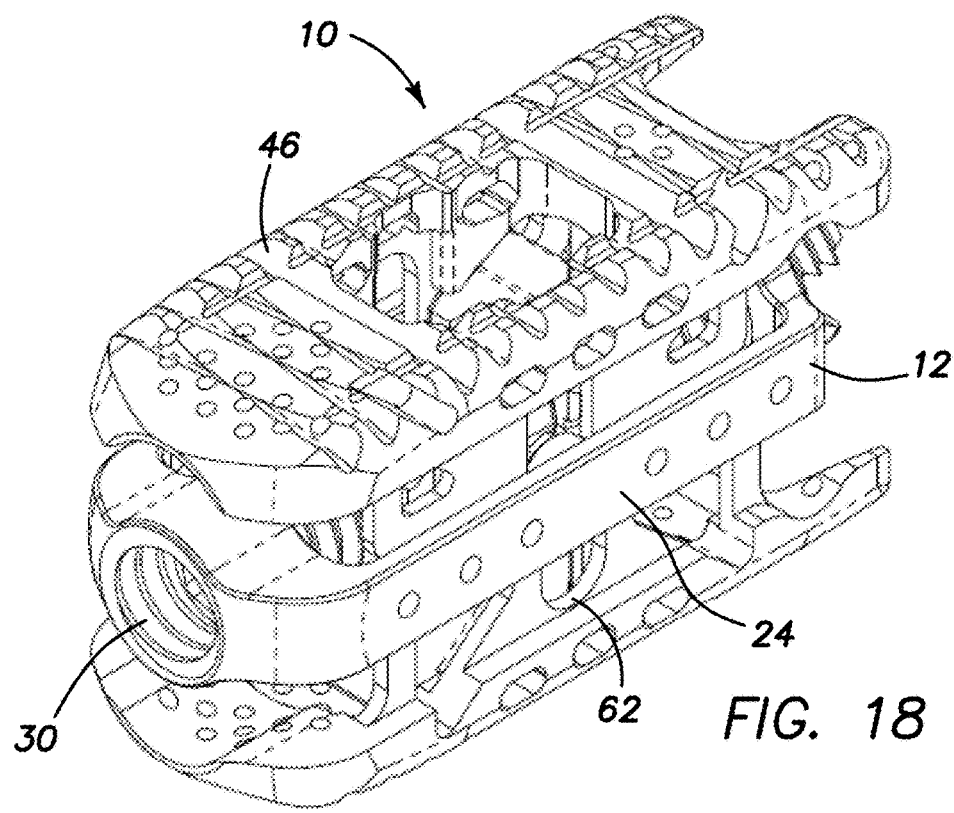
FIG. 18 is a top perspective view of an expandable interbody spacer in its high-profile configuration according to the present invention.
Figure 19:
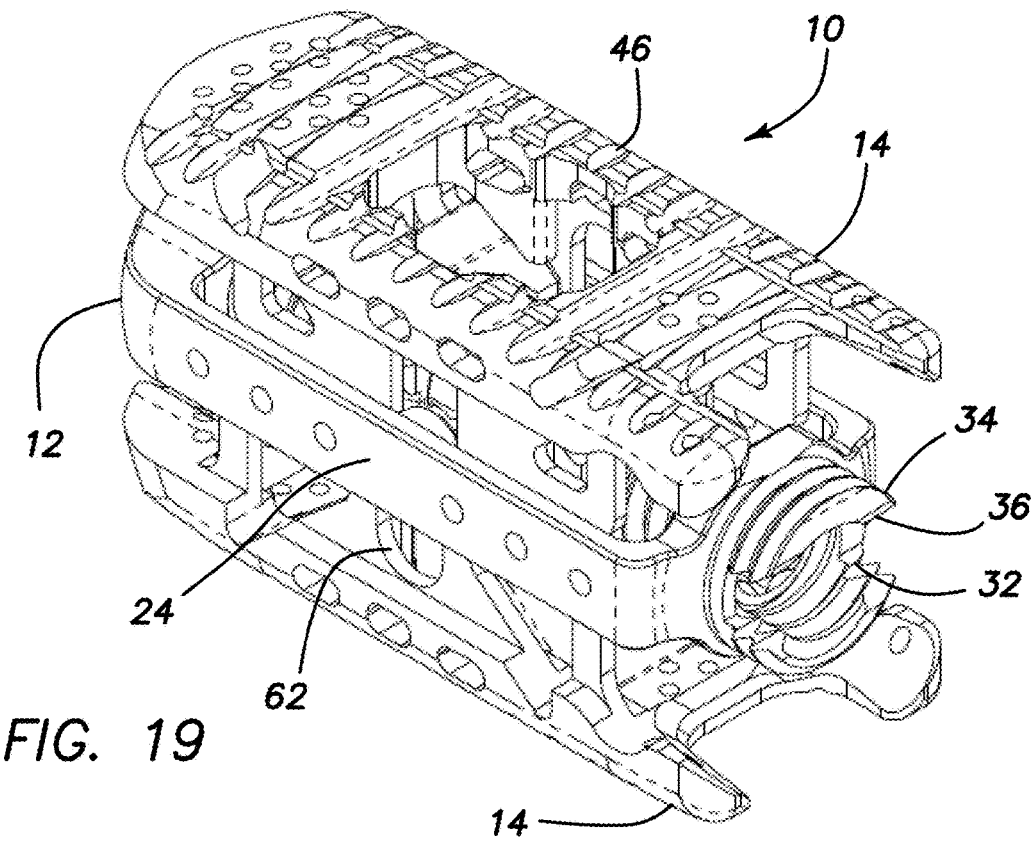
FIG. 19 is a top perspective view of an expandable interbody spacer in its high-profile configuration according to the present invention.
Figure 20:
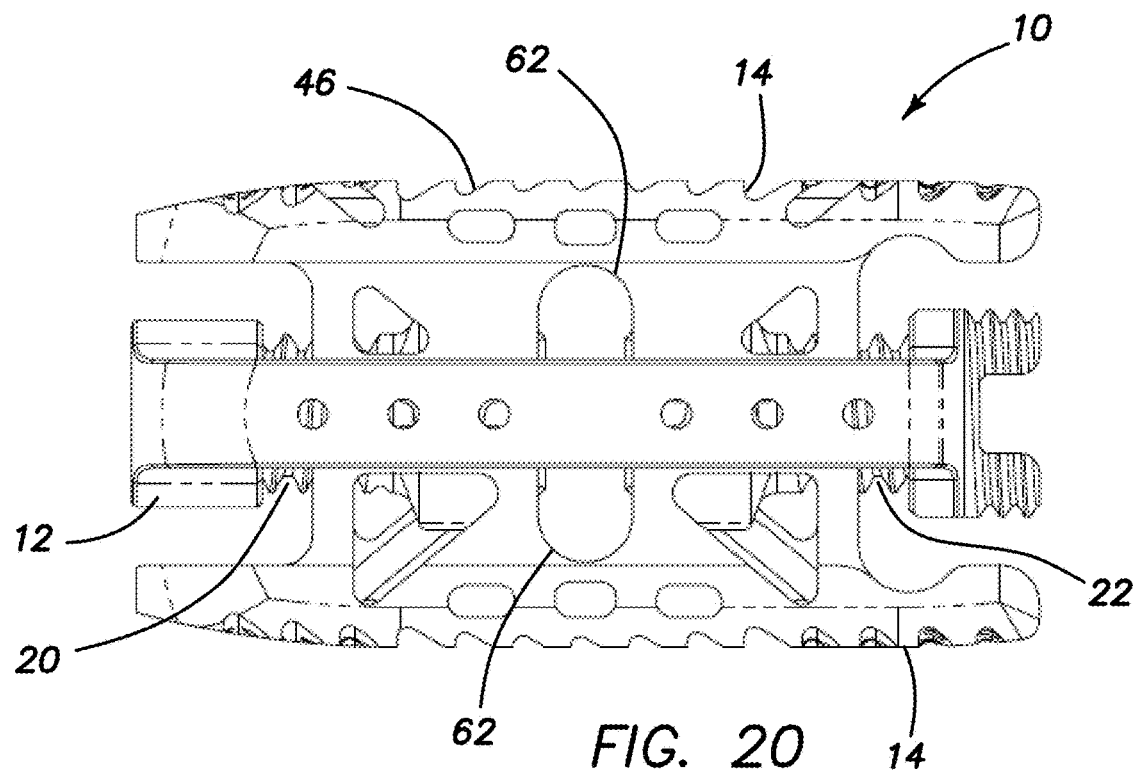
FIG. 20 is a side elevational view of the expandable interbody spacer of FIG. 18.
Figure 21:
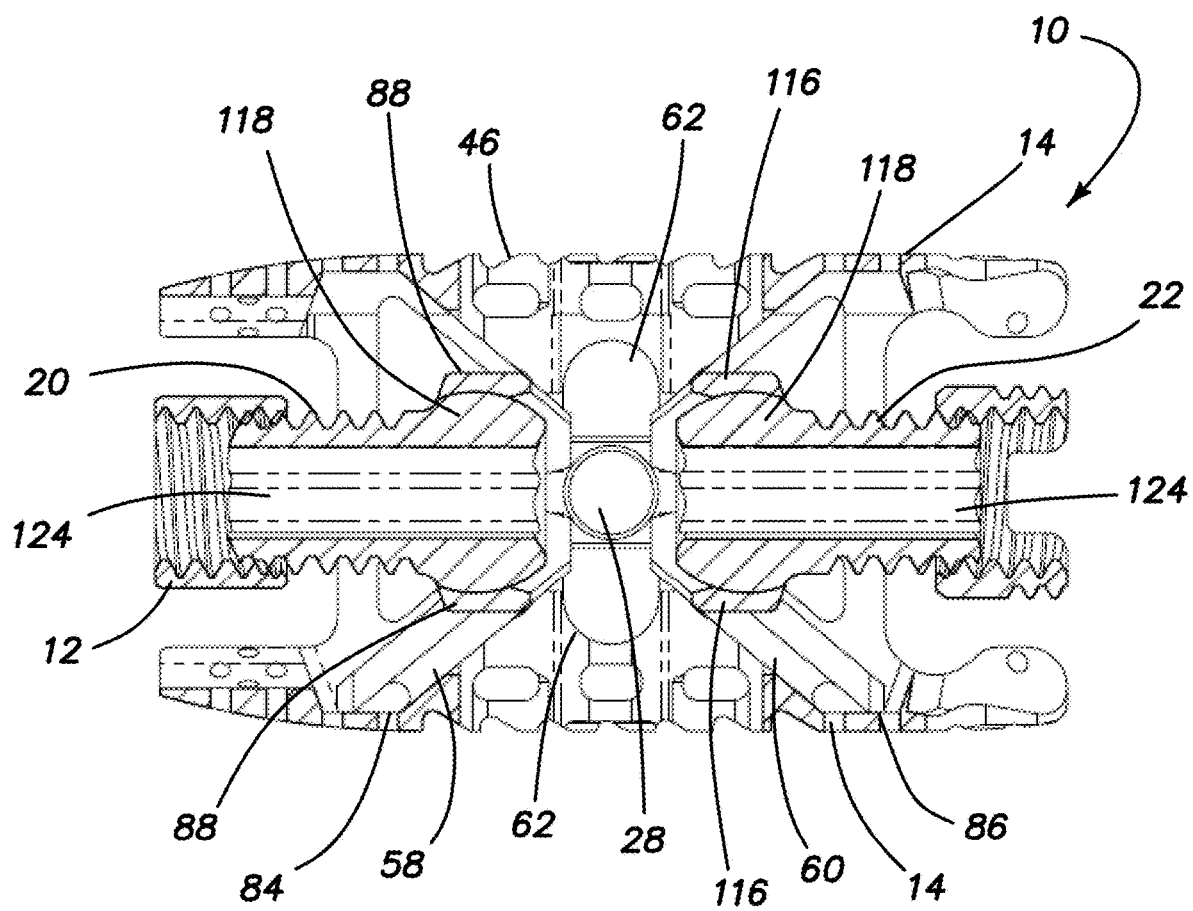
FIG. 21 is a cross-sectional view of the expandable interbody spacer of FIG. 18.
Figure 22:
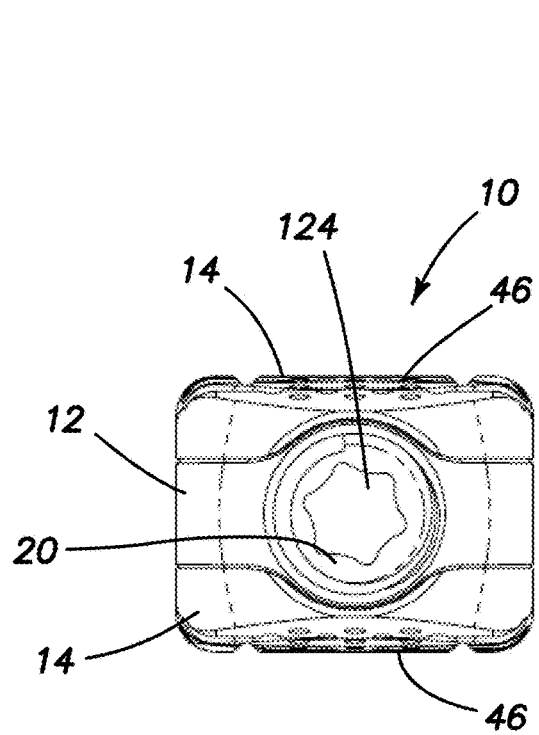
FIG. 22 is an anterior end view of an expandable interbody spacer in its low-profile configuration according to the present invention.
Figure 23:
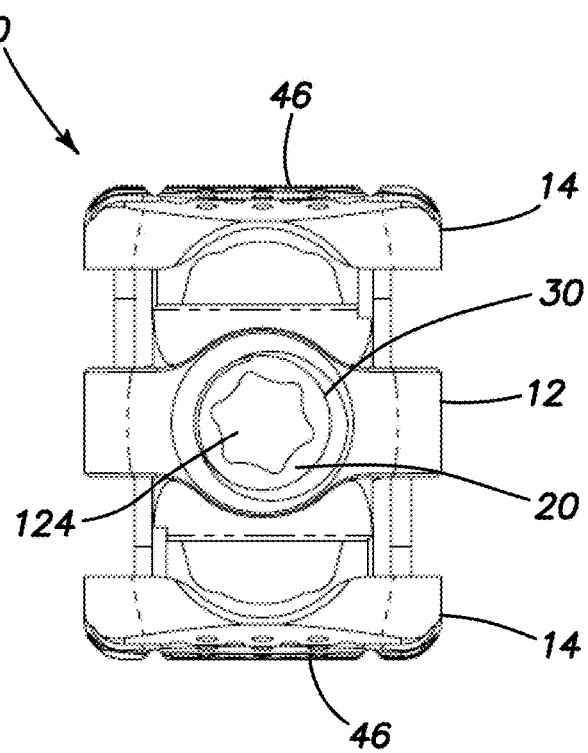
FIG. 23 is an anterior end view of an expandable interbody spacer in its high-profile configuration according to the present invention.
Figure 24:
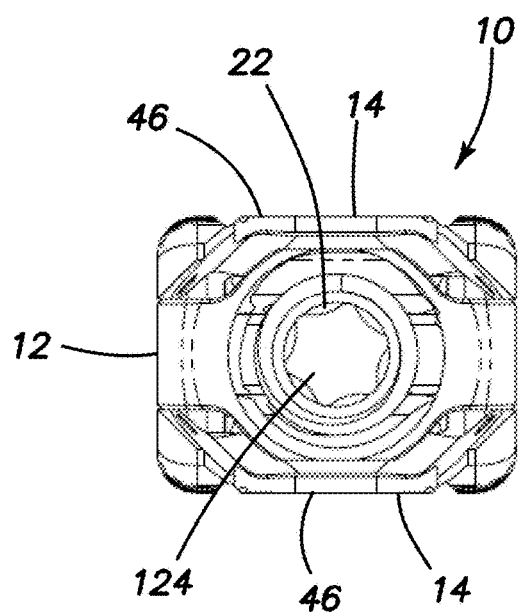
FIG. 24 is a posterior end view of an expandable interbody spacer in its low-profile configuration according to the present invention.
Figure 25:
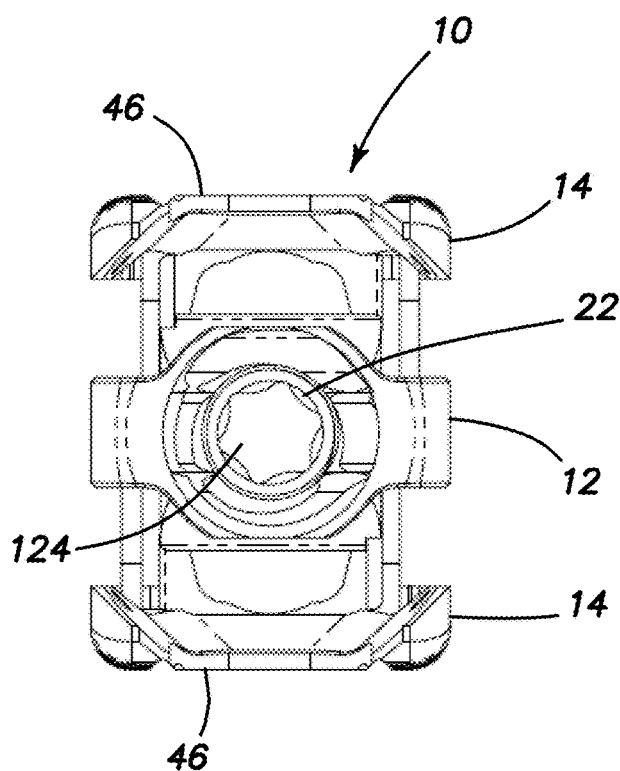
FIG. 25 is a posterior end view of an expandable interbody spacer in its high-profile configuration according to the present invention.

Turning now to FIG. 16, there is shown the driver instrument 23 according to the present invention. The driver 23 includes a handle 126 at the proximal end. The driver 23 further includes a proximal drive portion 128 having a length and distal drive portion 130 having a length separated by a middle portion 132 having a length. The handle 126 may include a neck portion 134 between the handle 126 and the proximal drive portion 128. The distal drive portion 130 is located at the distal end of the driver 23 and extends proximally toward the middle portion 132. The proximal drive portion 128 is located near the handle 126 and extends proximally from the middle portion 132 towards the handle 126 or neck portion 134 if a neck portion 134 is defined. The proximal and distal drive portions 128, 130 have a mating cross-section that is sized and configured to engage with drive bores 124 of the anterior and posterior drive screws 20, 22, respectively, in order to rotate the anterior and posterior drive screws 20, 22. The cross-sectional shape of the proximal and distal drive portions 128, 130 are uniform and extend along their entire respective lengths. The distal drive portion 130 has a cross-section that is sized and configured to also engage with the drive bore 124 of the posterior drive screw 22. In one variation, all of the drive bores 124 have the same cross-sectional shape and the drive portions 128, 130 have the same corresponding cross-sectional shape and, in another variation, have the same diameter. For example, in one variation, the drive bores 124 have a hexalobe shape as shown in FIGS. 14-15 and the driver 23 has proximal and distal drive portion 128, 130 that also have a hexalobe shape sized and configured to engage the drive screws 20, 22 for rotation. The diameters of the proximal and distal drive portions 128, 130 are the same to match the diameters of the drive bores 124 and are greater in diameter than the diameter of the middle portion 132. The middle portion 132 does not have an outer surface sized and configured to engage any drive bores 124 into rotation. In another variation, the middle portion has a smooth circular cross-section and middle diameter that is the same as the diameter or inner diameter of the drive bores 124. The diameter of the handle 126 is greater than the diameter of the drive portions 128, 130 and, if a neck portion 134 is provided, the neck portion 134 has a diameter greater than the drive portions 128, 130. The neck portion 134 does not have an outer surface or cross-sectional shape configured to engage any of the drive screws 20, 22. The handle 126 or neck portion 134 serves as an abutment or stop for the insertion of the driver 23. If there is no neck portion 134, the handle 126 will serve as an abutment. The distal drive portion 130 of the driver 23 is sized and configured such that it can be inserted first into the posterior drive screw 22 and passed distally into the spacer 10 into the anterior drive screw 20 until the neck portion 134 or handle 126, because of its larger diameter, abuts the proximal end of the posterior drive screw 20 or spacer 10 and, thereby, the driver 23 is prevented from further insertion into the spacer 10. The proximal drive portion 128, the middle portion 132 and the distal drive portion 130 altogether define the active portion 136 of the driver 23 and their combined lengths or the length of the active portion 136 is not longer than the length of the spacer 10. If the active length 136 of the driver 23 is longer than the spacer 10, the distal end of the driver 23 would extend beyond the length of the spacer 10 when the handle 126 is abutted at the proximal end and potentially impinge on surrounding tissue. Hence, the neck portion 134 serves as an abutment that simplifies the insertion of the driver 23 by allowing the user to insert the driver 23 until abutment is made with the neck portion without fear of the driver 23 extending beyond the distal end of spacer 10.

The driver 23 is configured such that the distal drive portion 130 engages the anterior drive screw 20 and the proximal drive portion 128 engages the posterior drive screw 22 simultaneously when the spacer 10 is in the collapsed, low-profile configuration in order to rotate both of the drive screws 20, 22 simultaneously. The driver 23 is also configured to be pulled back in the proximal direction such that the proximal drive portion 128 is disengaged from the posterior drive screw 22 while the distal drive portion 130 remains engaged with the anterior drive screw 20 to effect variable angulation of the anterior end of the spacer 10. When the spacer 10 is in the collapsed, low-profile configuration, the drive screws 20, 22 will be at the farthest distance apart from each other. Hence, the middle portion 132 is longer than the distance between the drive screws 20, 22 when in the collapsed low-profile configuration so that the driver 23 may be pulled back in the proximal direction to disengage the proximal drive portion 128 from the posterior drive screw 22 while the distal drive portion 130 still engages with the anterior drive screw 20. The length of the active portion 136 or the combined length of the distal drive portion 130, proximal drive portion 128 and middle portion 132 is approximately equal to the length of the spacer 10. The length of the proximal drive portion 128 is shorter than the length of the distal drive portion 130. Given these parameters and to reduce the torque required to rotate the drive screws 20, 22, the length of the distal drive portion 130 is approximately equal to the length of the anterior drive screw 20 and the length of the proximal drive portion 22 is shorter than the length of the posterior drive screw 22. In one variation, the distal drive portion 130 is equal to the length of the anterior drive screw 20, the proximal drive portion 128 is ⅘ the length of the posterior drive screw 22 and the middle portion 132 is ⅝ longer than the length of the distance between the two drive screws 20, 22 when the spacer 10 is in the collapsed low-profile configuration. The drive portions 128 and 130 are coaxial.

The expandable interbody spacer 10 is assembled by placing one endplate 14 such that the interior surface 48 faces upwardly defining a lower endplate 14. One anterior actuator segment 88 is placed into the anterior well 84 of the lower endplate 14 such that the anterior projection 72 of the lower endplate 14 is received inside the side channel 108 of the anterior actuator segment 88. One posterior actuator segment 116 is placed into the posterior well 86 of the lower endplate 14 such that the posterior projection 74 of the endplate 14 is received inside the side channel 108 of the posterior actuator segment 116. The anterior drive screw 20 is threaded into the distal threaded opening 30 of the housing 12 and the posterior drive screw 22 is threaded into the rear threaded opening 32. The guideposts 28 of the housing 12 are aligned with the slots 62 of the lower endplate 14. The drive screws 20, 22 may be threaded to adjust their alignment such that the ball heads 118 are received inside the inner surface 100 of the anterior and posterior actuator segments 88, 116. A second anterior actuator segment 88 is connected to the upper endplate 14 by inserting the anterior projection 72 into side channel 108 of the second anterior actuator segment 88. A second posterior actuator segment 116 is connected to the upper endplate 14 by inserting the posterior projection 74 into the side channel 108 of the second posterior actuator segment 116. The upper endplate 14 is aligned so that the slots 62 of the upper endplate 14 receive the guideposts 28 of the housing 12 and that the actuator segments 88, 116 connected to the upper endplate 14 cover the ball heads 118 of the drive screw 20, 22. Pressure is applied such that the overhangs 114 of the actuator segments 88, 116 snap over the ball heads 118.

In use, the present expandable interbody spacer 10 is inserted into the disc space between adjacent vertebral bodies. The spacers 10 of FIGS. 1-29 are generally configured for use as a PLIF cage in spinal surgical procedures. It is understood that novel features of the present invention can find application in different types of spacers including but not limited to interbody spacers for PLIF, TLIF, XLIF surgical procedures as well as other types of orthopedic implants.

Implanting the interbody spacer 10 involves removal, in whole or in part, of the disc material from the intervertebral space at the target vertebral level where the interbody spacer 10 will be implanted. The patient is oriented to provide some distraction of the disc space and to provide access to the spine. Additional distraction of the disc space and surrounding tissues may be needed to decompress the nerve roots, realign the anatomical axis of the spine, and restore disc space height at the particular target level. After disc material is removed, a clean space is achieved in which to place the device. The vertebral endplates may be further prepared using burrs, curettes and the like to abrade and clean the endplates to encourage bone regeneration.

A surgeon will then connect the spacer 10 for to an insertion instrument (not shown). The insertion instrument is aligned with the spacer 10 via the notches 36 and connected at the proximal end of the spacer 10 such that it is secured to the collar 34 by threadingly engaging the insertion instrument around the collar 34. The driver 23 is configured to be inserted into one or more of the anterior drive screw 20 and posterior drive screw 22 by aligning the distal and proximal drive portions within the selected one or more drive bores 124 as will be described in greater detail below. The surgeon uses the insertion instrument to grasp the spacer 10 and place it at the mouth of the intervertebral space in its low-profile configuration. The spacer 10 is moved and orientated into its proper location within the intervertebral space. Bone graft or other material may be placed inside the interior of the spacer 10 through the endplate openings 52 prior the insertion of the spacer 10 into the disc space. The bone graft material promotes ingrowth and improves blood supply in order to grow active and live bone from the adjacent spinal vertebrae to inter-knit with the spacer 10 and, thereby, eventually immobilize and fuse the adjunct spinal vertebrae.

The spacer 10 is placed such that the upper endplate 14 contacts the lower endplate of the upper vertebral body and the lower endplate 14 of the spacer 10 contacts the upper endplate of the lower vertebral body on either side of the target intervertebral space. The geometry of the teeth on the bone-engaging surface 46 provides resistance to migration of the spacer 10 while inside the target space. Other coatings and surface textures may also be provided on the spacer 10. When the spacer 10 is in position, the driver 23 is connected to the spacer 10 to deploy the spacer 10 into its expanded or high-profile configuration. The insertion instrument may be disconnected and removed when needed.

Turning now to FIGS. 17-25, uniform parallel expansion of the spacer 10 will now be described. The spacer 10 is inserted into the disc space while it is in an unexpanded, collapsed state. The unexpanded state is illustrated in FIGS. 1-4, 22 and 24. The distal end of the driver 23 is inserted into the drive bore 124 of the posterior drive screw 22 and moved in a distal direction relative to the spacer 10 until the distal drive portion 130 of the driver 23 is completely inserted into the drive bore 124 of the anterior drive screw 20 while the spacer 10 is in an unexpanded, low profile configuration as shown in FIGS. 17A-17B. When the distal drive portion 130 is aligned with the anterior drive screw 20, such that the length of the distal drive portion 130 is resident within the length of the anterior drive screw 20, the proximal drive portion 128 will be advantageously aligned with the posterior drive screw 22 such that the hexalobe cross-section of the posterior drive screw 22 engages the hexlobe cross-section of the drive bore 124. The drive bore 124 is formed along the entire length of each drive screw 20, 22 and each drive screw 20, 22 has proximal and distal openings. The insertion of the driver 23 into the spacer 10 is facilitated advantageously by the drive screws 20, 22 and their respective drive bores 124 being aligned with each other coaxially along a drive axis. Because of the corresponding hexalobe cross-sectional shape of the drive bores 124 and drive portions, the driver 23 is easily inserted into both the anterior and posterior drive screws 20, 22 with a minimum of rotation of the driver 23 for alignment purposes before the distal drive portion 128 enters the anterior drive screw 20. Furthermore, insertion of the driver 23 into a position for parallel expansion is facilitated by the neck portion 134 of the driver 23 which has a diameter larger than the diameter of the drive bore 124. The user simply inserts the driver 23 until the neck portion 134 abuts against the posterior drive screw 22. If a driver 23 variation without a neck portion 134 is used, the handle 126, having a larger diameter than the posterior drive screw 22, will abut the drive screw 22. The neck portion 134 advantageously allows the driver 23 to have a longer in length while at the same time providing a low-profile and a substantial handle 126 of increased diameter to the driver 23 to fit a surgeon's hand. The active portion 136 of the driver 23 is approximately equal to the length of the spacer 10. The neck portion 134 or handle 126, if an intermediate diameter neck portion 134 is not employed, advantageously serves as a stop preventing insertion of the driver 23 beyond a distance of approximately the length of the spacer 10. This stop advantageously prevents the distal end of the driver 23 from protruding beyond the approximate distal end of the spacer 10. Furthermore, the neck portion 134 allows the surgeon to easily and quickly insert the driver 23 into the spacer 10 all the way until abutment is made with the enlarged diameter of the neck portion 134 or handle 126. Also, advantageously, the interior of the spacer 10 provides a clear pathway for the passage of the driver 23 between the two drive screws 20, 22 as the spacer 10 is configured so that there are no impeding mechanical or anatomical structures that would interfere with clear passage of the driver 23. When the driver 23 is inserted for parallel expansion as shown in FIG. 17B, the distal drive portion 130 will be automatically aligned within the drive bore 124 of the anterior drive screw 20 and the proximal drive portion 128 will be automatically aligned within the drive bore 124 of the posterior drive screw 22 and the middle portion 132 will be located between the two drive screws 20, 22. As mentioned previously, the length of the distal drive portion 130 is approximately the same length as the length of the anterior drive screw 20 to provide the user with maximum torqueing advantage. The length of the proximal drive portion 128 is shorter than the length of the posterior drive screw 22 and the middle portion 132 is longer than the distance between the drive screws 20, 22 when the spacer 10 is in the unexpanded. When the driver 23 is in position for parallel expansion as shown in FIG. 17B, the driver 23 is rotated in one of a clockwise direction or counterclockwise direction to bring the spacer 10 into an expanded state. When the driver 23 is rotated, the posterior drive screw 22 is rotated. As the posterior drive screw 22 is rotated, the threads on the threaded shank 120 engage the complementary threads on the rear threaded opening 32 of the housing 12 allowing the posterior drive screw 22 to translate distally with respect to the housing 12 due to the right-handedness of the threads of the posterior drive screw 22 as viewed from the proximal end of the spacer 10. As the posterior drive screw 22 moves distally, it moves the posterior actuator 18 distally along with it. The leading surfaces 90 of upper and lower posterior actuator segments 116 will contact the posterior ramps 60 and slide along the posterior ramps 60 to wedge the upper and lower endplates 14 apart causing the endplates 14 at the proximal end to separate and increase in height. Simultaneously, when the driver 23 is rotated in the same direction, the threads on the threaded shank 120 of the anterior drive screw 20 engage the complementary threads on the distal threaded opening 30 of the housing 12 causing the anterior drive screw 20 to move in a proximal direction with respect to the housing 12 due to the left-handedness of the threads of the anterior drive screw 20. As the anterior drive screw 20 moves proximally, it moves the anterior actuator 16 proximally along with it. The leading surfaces 90 of upper and lower anterior actuator segments 88 contact the anterior ramps 58 and slide along the anterior ramps 58 to wedge the upper and lower endplates 14 apart causing the endplates 14 at the distal end of the spacer 10 to separate and increase in height. Hence, the drive screws 20, 22 advantageously move in opposite directions from each other, in particular, towards each other to effect expansion of the endplates 14 increasing the distance of the spacer 10 uniformly on both sides simultaneously as both the upper and lower endplates 14 move away from the housing 12 when the driver 23 is rotated in the same direction. The spacer 10 in a condition of uniform parallel expansion is shown in FIGS. 18-21, 23 and 25. The degree of expansion is variable with rotation of the driver 23 and the surgeon may advantageously select the desired height of the spacer 10 according to patient anatomy by rotating the driver 23 to expand the spacer 10 as much as needed. Also, rotation of the driver 23 in the opposite direction reduces the height of spacer 10 at both ends simultaneously. The forces exerted onto the endplates 14 from the weight of the spinal column are distributed along two drive screws 20, 22 and, hence, there is less friction on the threads of one drive screw requiring less torque to increase or decrease the height of the spacer 10. Incremental rotation in either direction increases or decreases the height as needed. Both the upper and the lower endplates 14 are wedged apart by both actuators 16, 18 and the endplates 14 move away from the longitudinal axis of the spacer 10 uniformly. The ball heads 118 of the drive screws 20, 22 face the center of the spacer 10 and their threaded shafts 120 face the distal and proximal ends of the spacer 10, respectively. Advantageously, both drive screws 20, 22 can be rotated from the insertion end which is the proximal end of the spacer 10.

Figure 27:
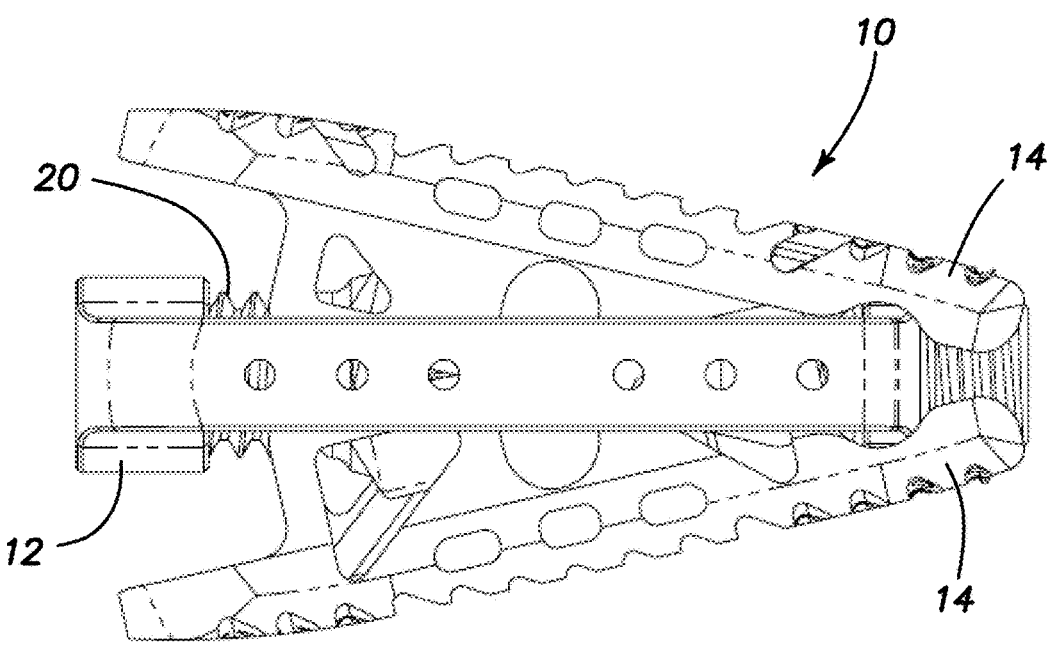
FIG. 27 is a side elevational view of an expandable interbody spacer in its anterior angulated configuration according to the present invention.
Figure 28:
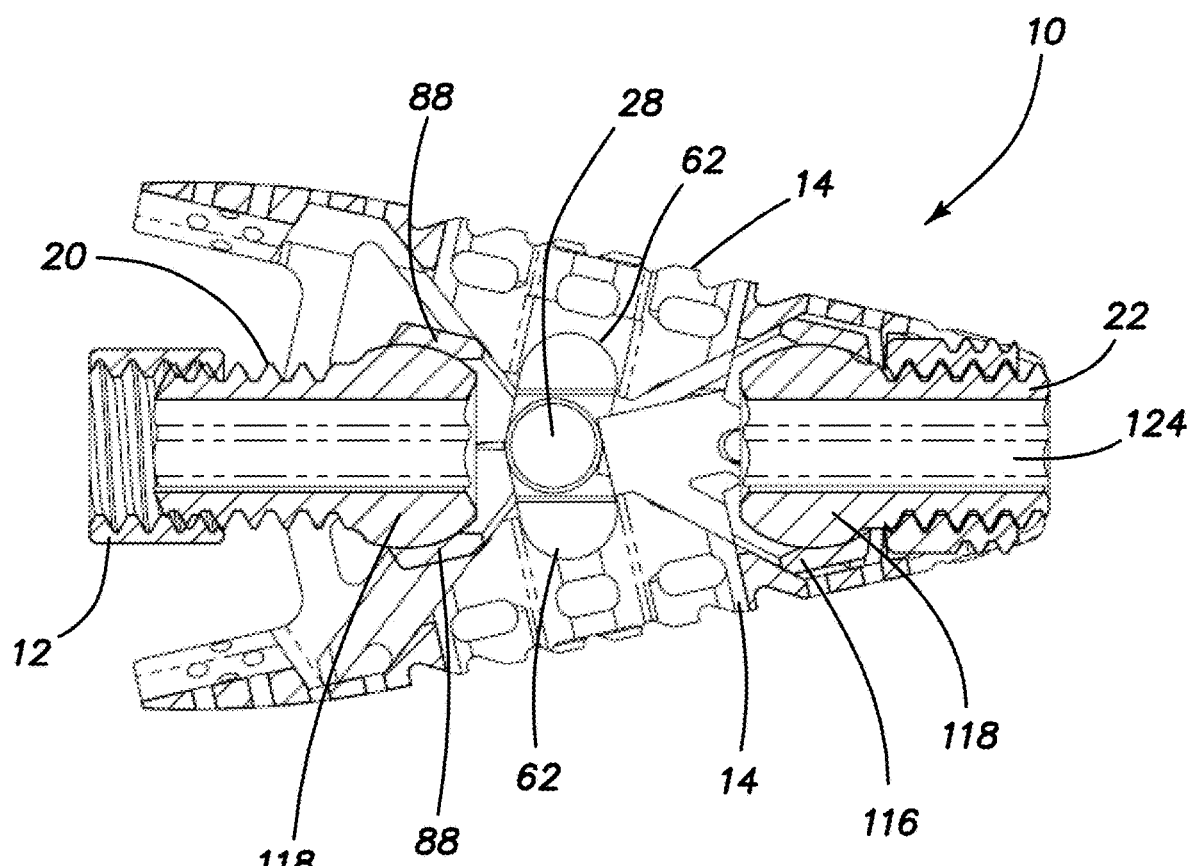
FIG. 28 is a cross-sectional view of the expandable interbody spacer of FIG. 27.

Turning now to FIGS. 26-28, anterior angular expansion of the spacer 10 will now be described. When the spacer 10 is inserted into the anatomical disc space while it is in an unexpanded, collapsed state, typically with the use of an insertion instrument (not shown) aligned with the notches 36 and threaded to the collar 32 of the housing 12. The spacer 10 is inserted in its unexpanded state in order to provide the least invasive approach. Of course, according to surgeon preference, the disc space may be distracted prior to insertion of the spacer 10 and the spacer 10 may be in a semi-expanded configuration, either in angled or parallel expansion. The spacer 10 may be inserted into the disc space while spacer 10 is in a posterior angled configuration in order to help distract the disc space during insertion of the spacer 10. The posterior angled configuration will be described in greater detail below. The unexpanded state is illustrated in FIGS. 1-4, 22 and 24. While the spacer 10 is, preferably in an unexpanded, low profile configuration, the distal end of the driver 23 is mated and inserted into the drive bore 124 of the posterior drive screw 22 and moved in a distal direction relative to the spacer 10 until the distal drive portion 130 of the driver 23 is inserted into the drive bore 124 of the anterior drive screw 20. The driver 23 is not inserted all the way until abutment with the neck portion 134 is achieved. Instead, insertion of the driver 23 is arrested at a position prior to the proximal drive portion 128 entering the posterior drive screw 22 so that the hexalobe-shaped, bore-engaging cross-section of the proximal drive portion 128 is not engaged with the hexalobe-shaped, driver-engaging cross-section of the drive bore 124 of the posterior drive screw 22 as shown in FIGS. 26A-26B. This partial insertion leaves the posterior drive screw 22 completely disengaged from the driver 23 and only part of the length of the distal drive portion 130 engaged with the anterior drive screw 20. As a result, when the driver 23 is rotated in one of a clockwise direction or counterclockwise direction to bring the spacer 10 into an expanded state, the anterior drive screw 20 will only be rotated and the posterior drive screw 22 will not be rotated because in the anterior expansion position, the middle portion 132 having a smaller diameter or a smooth, non-engaging, circular cross-section will be resident along the entire length of the posterior drive screw 20. Hence, when the driver 23 is rotated, the posterior drive screw 22 will not be rotated and, thereby, remain stationary with respect to the housing 12. However, when the driver 23 is rotated, the anterior drive screw 20 will move in a proximal direction with respect to the housing 12 due to the left-handedness of the threads of the anterior drive screw 20. As the anterior drive screw 20 moves proximally, it moves the anterior actuator 16 proximally along with it. The leading surfaces 90 of the upper and lower anterior actuator segments 88 will contact the anterior ramps 58 and slide along the anterior ramps 58 to wedge the upper and lower endplates 14 apart bringing the anterior/distal end of the spacer 10 into an expanded condition forming an angle relative to the un-expanded height of the posterior/proximal end. In anterior angular expansion, the anterior drive screw 20 moves proximally. Only the distal end of the spacer 10 will increase in height as both the upper and lower endplates 14 are wedged apart uniformly oppositely from the longitudinal axis of the spacer 10; whereas, the posterior/proximal end of the spacer 10 will remain in an unexpanded state creating an angle of the upper endplate 14 and lower endplate 14 with respect to the housing 12. The spacer 10 in anterior angular expansion is shown in FIGS. 27 and 28. The degree of angulation or angular expansion is variable and incremental with incremental rotation of the driver 23 and the surgeon may advantageously select the desired height of the anterior end of the spacer 10 according to patient anatomy by rotating the driver 23 only as much as is needed to expand and angulate the spacer 10 as desired by the surgeon. The range of angulation of each endplate 14 is approximately between 0 and 15 degrees from the horizontal. To collapse or readjust the spacer 10, the driver 23 can be rotated in the opposite direction to reduce the height and angle of the spacer 10. If needed the driver 23 can then again be rotated to increase the height again and repeated as needed for surgeon satisfaction. Variable and incremental rotation reduces the height as needed. Both the upper and the lower endplates 14 are wedged apart by the anterior actuator 16 and both of the upper and lower endplates 14 move away from the longitudinal axis of the spacer 10 uniformly at the anterior end for anterior angular expansion. The driver 23 may be color coded with a color band around the driver 23 at a location to denote the distance to insert the driver 23 for anterior angular expansion. The driver 23 may also be marked with an arrow, a line or other indicia to denote the insertion limit for anterior angular expansion.

Figure 29:
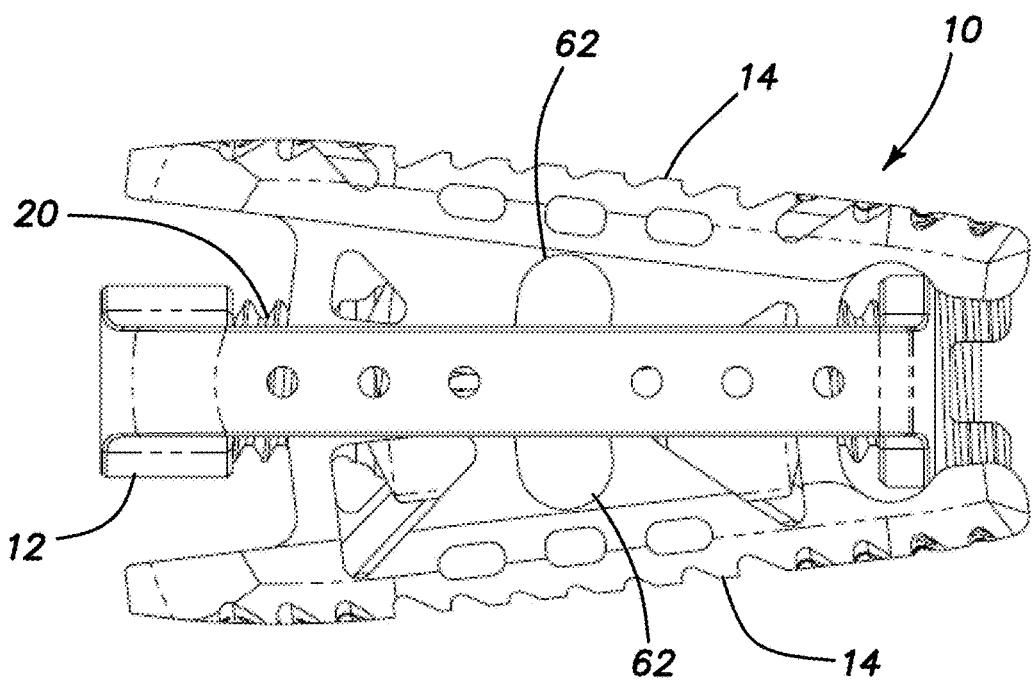
FIG. 29 is a side elevational view of an expandable interbody spacer in its combined configuration of anterior angulation and parallel expansion according to the present invention.
Figure 30:
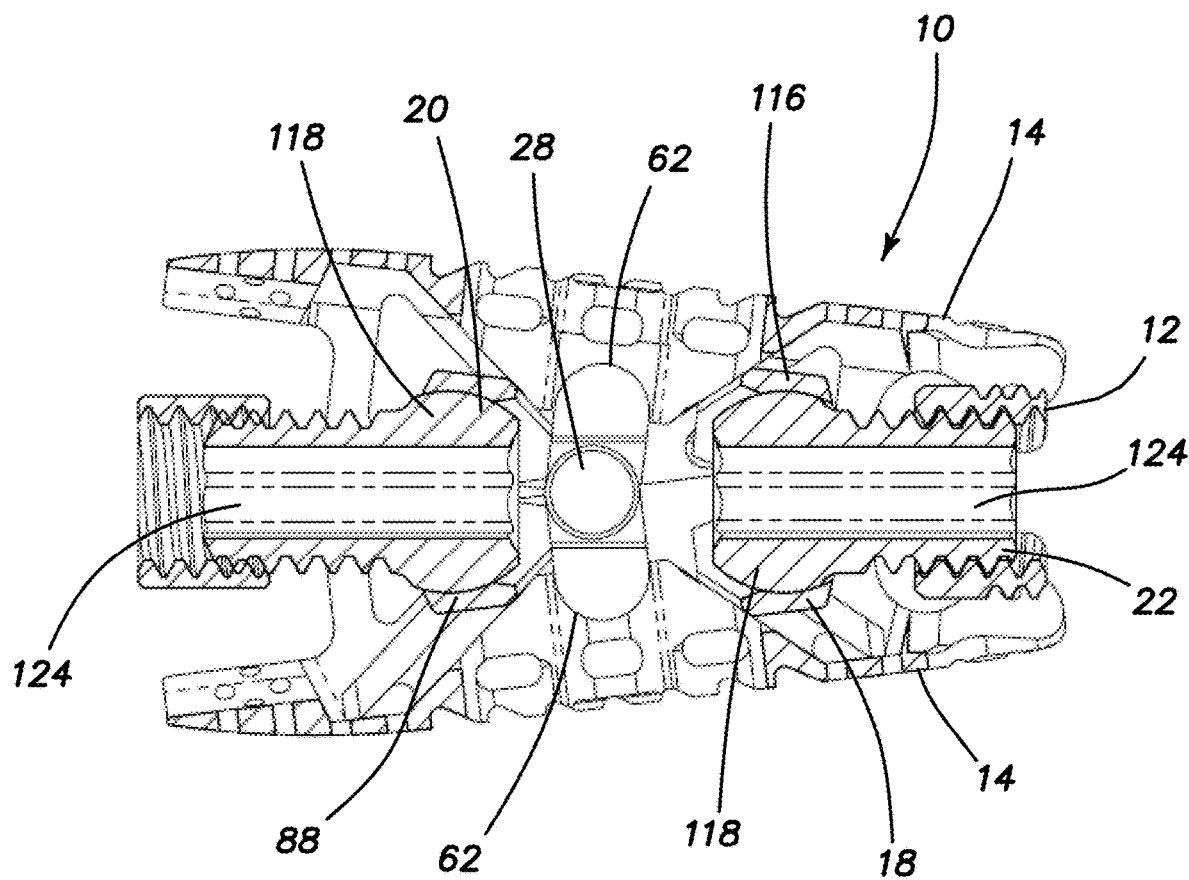
FIG. 30 is a cross-sectional view of the expandable interbody spacer of FIG. 29.

Turning now to FIGS. 29-30, anterior angular expansion may also be combined with uniform parallel expansion in which the posterior drive screw 22 is rotated to increase the height of the proximal end prior to or subsequent to anterior angular expansion in which the driver 23 is positioned such that the distal drive portion 130 engages only with the posterior drive screw 22 as shown in FIGS. 31A-31B. Alternatively, the driver 23 may be positioned as shown in FIGS. 17A-17B for uniform parallel expansion prior to or subsequent to being positioned for anterior angular expansion as shown in FIGS. 26A-26B. The combination of anterior angular expansion with parallel expansion results in the distal/anterior end having an overall greater height than the proximal/posterior end of the spacer 10 resulting in an expanded and angulated condition of expansion. In essence, customized as well as variable uniform parallel and angular expansion is made possible by positioning the driver 23 to rotate one or both of the anterior and posterior drive screws 20, 22 providing the greatest flexibility in angulation and expansion.

Figure 32:
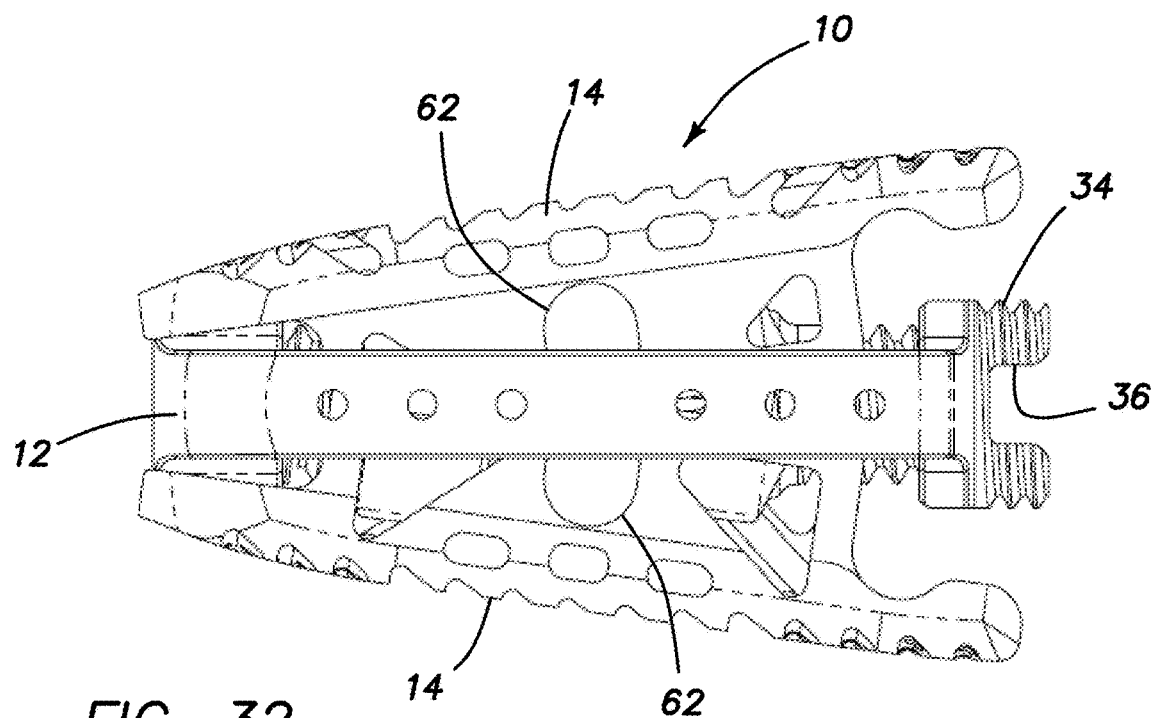
FIG. 32 is a side elevational view of an expandable interbody spacer in its posterior angulated configuration according to the present invention.
Figure 33:
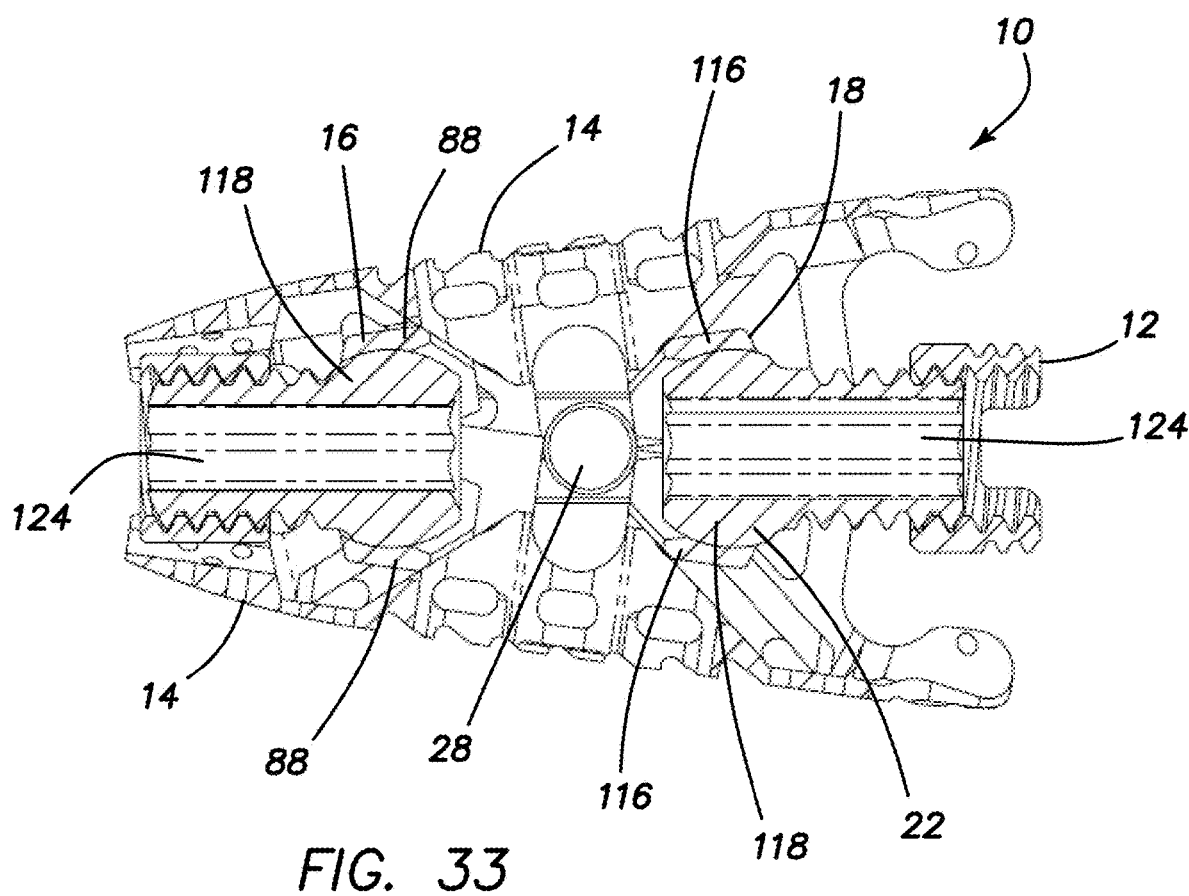
FIG. 33 is a cross-sectional view of the expandable interbody spacer of FIG. 32.

Turning now to FIGS. 31-33, posterior angular expansion of the spacer 10 will now be described. The spacer 10 is inserted into the anatomical disc space while it is in an unexpanded, collapsed state. The unexpanded state is illustrated in FIGS. 1-4, 22 and 24. While the spacer 10 is in an unexpanded, low profile configuration, the distal end of the driver 23 is inserted into the drive bore 124 of the posterior drive screw 22 and moved in a distal direction relative to the spacer 10 until, preferably, the entire length of the distal drive portion 130 is inserted into the drive bore 124 of the posterior drive screw 22. A color-coded marker or other indicia may be provided on the driver 23 to indicate to the user where to stop insertion of the driver 23 for posterior angular expansion. The driver 23 is not inserted all the way until abutment with the neck portion 134 is achieved. Instead, insertion of the driver 23 is arrested when the distal drive portion 130 is engaged with the posterior drive screw 22, in particular, when the hexalobe-shaped, bore-engaging cross-section of the distal drive portion 130 is engaged with the hexalobe-shaped, driver-engaging cross-section of the drive bore 124 of the posterior drive screw 22 as shown in FIGS. 31A-31B. This partial insertion of the driver 23 leaves the anterior drive screw 20 completely disengaged from the driver 23. As a result, when the driver 23 is rotated in one of a clockwise direction or counterclockwise direction to bring the spacer 10 into an expanded state, the posterior drive screw 22 will only be rotated and the anterior drive screw 22 will not be rotated When the driver 23 is rotated in this position, the posterior drive screw 22 moves in a distal direction with respect to the housing 12 due to the right-handedness of the threads of the posterior drive screw 20. As the posterior drive screw 22 moves distally, it moves the posterior actuator 18 distally along with it. The leading surfaces 90 of the upper and lower posterior actuator segments 116 will contact the posterior ramps 60 and slide along the posterior ramps 60 to wedge the upper and lower endplates 14 apart increasing the distance between the endplates 12 at the posterior end bringing the posterior/distal end of the spacer 10 into an expanded angular condition. In posterior angular expansion, the posterior drive screw 22 moves distally. Only the proximal end of the spacer 10 will increase in height as both the upper and lower endplates 14 are wedged apart uniformly oppositely from the longitudinal axis of the spacer 10; whereas, the anterior/distal end of the spacer 10 will remain in an unexpanded state creating an angle of the upper endplate 14 and lower endplate 14 with respect to the horizontal housing 12. The spacer 10 in a condition of posterior angular expansion is shown in FIGS. 32 and 33. The degree of angulation or angular expansion is variable with rotation of the driver 23 and the surgeon may advantageously select the desired height of the posterior end of the spacer 10 according to patient anatomy by rotating the driver 23 only as much as is needed to expand and angulate the spacer 10 as desired by the surgeon. The range of angulation of each endplate 14 is approximately between 0 and 15 degrees from the horizontal. To collapse or readjust the spacer 10, the driver 23 can be rotated in the opposite direction to reduce the height and angle of the spacer 10. If needed the driver 23 can then again be rotated to increase the height again and repeated as needed for surgeon satisfaction. Variable rotation increases or reduces the height as needed. Both the upper and the lower endplates 14 are wedged apart by the posterior actuator 18 and both of the upper and lower endplates 14 move away from the longitudinal axis of the spacer 10 uniformly at the posterior end for posterior angular expansion.

Figure 34:
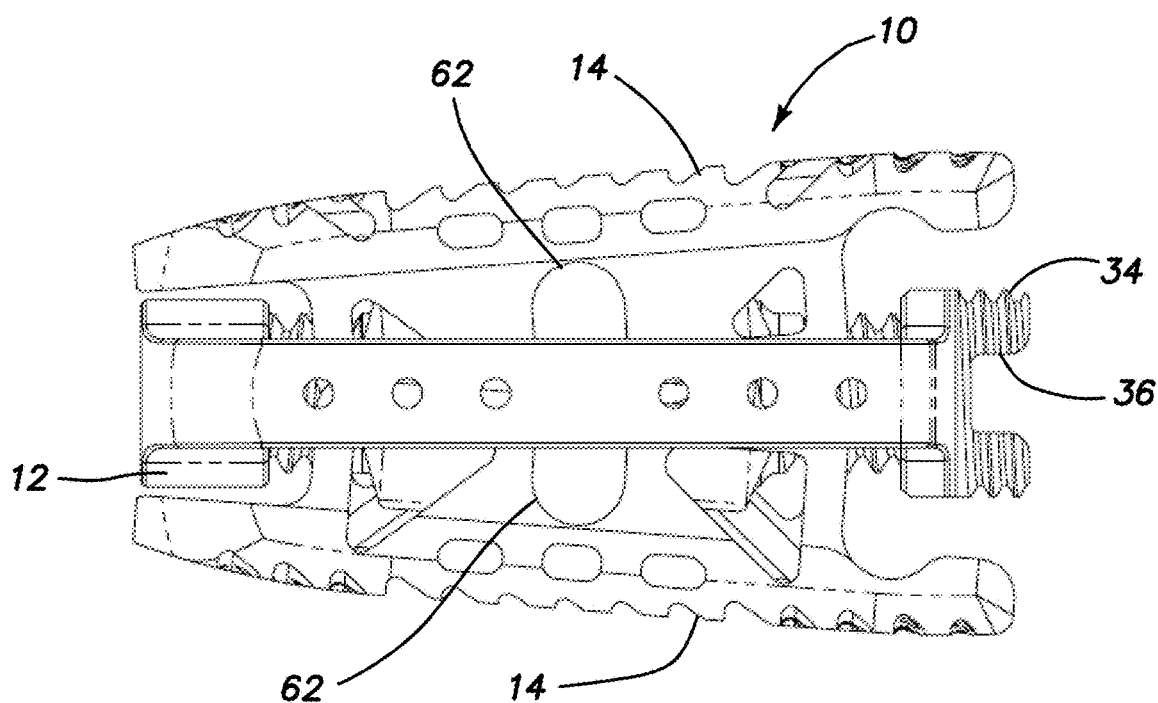
FIG. 34 is a side elevational view of an expandable interbody spacer in its combined configuration of posterior angulation and parallel expansion according to the present invention.
Figure 35:
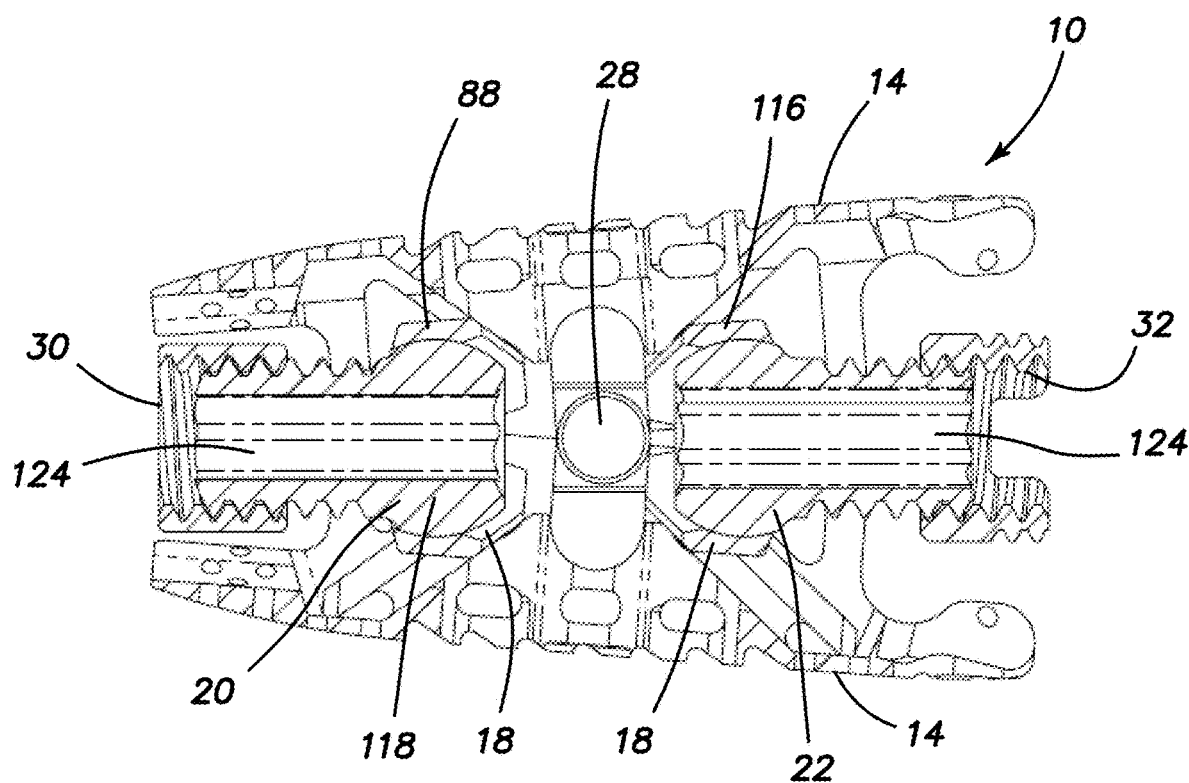
FIG. 35 is a cross-sectional view of the expandable interbody spacer of FIG. 34.

Turning now to FIGS. 34-35, posterior angular expansion may also be combined with uniform parallel expansion in which the anterior drive screw 20 is rotated to increase the height of the distal end prior to or subsequent to posterior angular expansion in which the driver 23 is positioned such that the distal drive portion 130 engages only with the anterior drive screw 22 as shown in FIGS. 26A-26B. Alternatively, the driver 23 may be positioned as shown in FIGS. 17A-17B for uniform parallel expansion prior to or subsequent to being positioned for posterior angular expansion as shown in FIGS. 31A-31B. The combination of posterior angular expansion with parallel expansion results in the proximal/posterior end having an overall greater height than the distal/anterior end of the spacer 10 resulting in an expanded and angulated condition of expansion. In essence, customized as well as variable uniform parallel and angular expansion is made possible by positioning the driver 23 to rotate one or both of the anterior and posterior drive screw 20, 22 providing the greatest flexibility in angulation and expansion. Each of the posterior and anterior ends may be expanded and/or angled independently to a height or angle as desired with incremental rotation in either direction to increase or decrease the angle and/or height with the use of one driver that is positioned variably along the longitudinal axis to effect the different states of expansion/angulation.

The expandable interbody spacer 10 is made of any suitable biocompatible material. The expandable interbody spacer 10 may be made from any one or combination of one or more metal such as titanium, ceramic, polymer such as polyether ether ketone (PEEK), carbon fiber reinforced polymer, biomaterial including but not limited to any of a number of biocompatible implantable polymers including PEKK, PEKEK, polyetheretherketone (PEEK) being preferred, titanium ceramic, bone or other material etc. The present invention can be employed and is suitable for use anywhere along the spine including but not limited to cervical, thoracic, lumbar or sacral or between other bony structures outside of the spinal region. Embodiments of the present invention are standalone interbody devices which may be designed in the general style of a TLIF device, PLIF device, ALIF or other device. In addition, the size and/or shape of the basic embodiments disclosed herein may be adapted by one skilled in the art for use in various levels of the spine, namely the cervical spine, thoracic spine and the lumbar spine. Thus, while various embodiments herein may be described by way of example with respect to the lumbar spine such disclosures apply with equal weight to the other levels of the spine.

It is understood that various modifications may be made to the embodiments of the interbody spacer disclosed herein. Therefore, the above description should not be construed as limiting, but merely as exemplifications of preferred embodiments. Those skilled in the art will envision other modifications within the scope and spirit of the present disclosure.

We claim:

1. An expandable interbody spacer having a longitudinal axis, a proximal end and a distal end, comprising:
   a housing having two sides interconnected by a distal endwall and a proximal endwall defining a hollow interior; the distal endwall having a threaded distal opening and the proximal endwall having a threaded proximal opening;
   an upper endplate and a lower endplate each having a posterior end and an anterior end, a bone-engaging surface and an interior surface opposite to the bone-engaging surface; the interior surface of each of the upper and lower endplates having an anterior ramp surface extending at an angle with respect to the interior surface and a posterior ramp surface extending at an angle with respect to the interior surface;

an anterior actuator located between the interior surfaces of the upper endplate and the lower endplate near the distal end of the spacer; the anterior actuator comprising an upper anterior actuator segment and a lower anterior actuator segment; the upper anterior actuator segment having a curved inner surface and an angled leading surface for contact with the anterior ramp surface of the upper endplate; the lower anterior actuator segment having a curved inner surface and an angled leading surface for contact with the anterior ramp surface of the lower endplate;

a posterior actuator located between the interior surfaces of the upper endplate and the lower endplate near the proximal end of the spacer; the posterior actuator comprising an upper posterior actuator segment and a lower posterior actuator segment; the upper posterior actuator segment having a curved inner surface and an angled leading surface for contact with the posterior ramp surface of the upper endplate; the lower posterior actuator segment having a curved inner surface and an angled leading surface for contact with the posterior ramp surface of the lower endplate;

an anterior drive screw comprising a proximal ball head connected to a distal threaded shank; the proximal ball head of the anterior drive screw being located between the curved inner surfaces of the upper and lower anterior actuator segments; the distal threaded shank being threadingly connected to the threaded distal opening; the anterior drive screw having an anterior drive bore extending from a proximal opening along a longitudinal drive axis; and a posterior drive screw comprising a proximal threaded shank connected to a distal ball head; the distal ball head of the posterior drive screw being located between the curved inner surfaces of the upper and lower posterior actuator segments; the proximal threaded shank being threadingly connected to the threaded proximal opening; the posterior drive screw having a posterior drive bore extending along the longitudinal drive axis between a proximal opening in the threaded shank and a distal opening in the distal ball head;

wherein rotation of the posterior drive screw in a first direction relative to the proximal end of the spacer around the longitudinal drive axis translates the posterior drive screw distally to wedge apart and expand the distance between the posterior ends of the upper and lower endplates;

wherein rotation of the anterior drive screw in the first direction relative to the proximal end of the spacer around the longitudinal drive axis translates the anterior drive screw proximally to wedge apart and expand the distance between the anterior ends of the upper and lower endplates;

wherein rotation of the posterior drive screw in a second direction relative to the proximal end of the spacer around the longitudinal drive axis translates the posterior drive screw proximally to reduce the distance between the posterior ends of the upper and lower endplates; and wherein rotation of the anterior drive screw in the second direction relative to the proximal end of the spacer around the longitudinal drive axis translates the anterior drive screw distally to reduce the distance between the anterior ends of the upper and lower endplates.

2. The expandable interbody spacer of claim 1 wherein the posterior and anterior drive screws are simultaneously and independently rotatable.

3. The expandable interbody spacer of claim 1 wherein the posterior and anterior drive screws are simultaneously and independently rotatable from the proximal end of the spacer.

4. The expandable interbody spacer of claim 1 wherein the proximal threaded shank of the posterior drive screw has threads opposite in direction from threads of the distal threaded shank of the anterior drive screw.

5. The expandable interbody spacer of claim 1 wherein the upper and lower anterior actuator segments snap around the proximal ball head of the anterior drive screw to capture the proximal ball head between the curved inner surfaces such that the anterior drive screw is rotatable relative to the anterior actuator; and wherein the upper and lower posterior actuator segments snap around the distal ball head of the posterior drive screw to capture the distal ball head between the curved inner surfaces such that the posterior drive screw is rotatable relative to the posterior actuator.

6. The expandable interbody spacer of claim 1 wherein the proximal ball head of the anterior drive screw is spherical in shape and the inner surfaces of the upper and lower anterior actuator segments together define a corresponding spherical shape; and wherein the distal ball head of the posterior drive screw is spherical in shape and the inner surfaces of the upper and lower posterior actuator segments together define a corresponding spherical shape.

7. The expandable interbody spacer of claim 1 wherein each of the upper and lower endplates includes first and second side rails extending from the interior surface; and wherein the anterior and posterior ramp surfaces of each of the upper and lower endplates are formed between the first and second side rails.

8. The expandable interbody spacer of claim 1 wherein the longitudinal drive axis is coaxial with the longitudinal axis of the spacer.

9. The expandable interbody spacer of claim 1 wherein the leading surfaces of the upper and lower anterior actuator segments face toward the proximal end and the leading surfaces of the upper and lower posterior actuator segments face toward the distal end.

10. The expandable interbody spacer of claim 1 wherein the leading surfaces of the upper and lower anterior actuator segments are angled away from each other toward the distal end of the spacer and the leading surfaces of the upper and lower posterior actuator segments are angled away from each other toward the proximal end of the spacer.

11. The expandable interbody spacer of claim 1 wherein the first direction is clockwise relative to the proximal end of the spacer, and wherein the second direction is counterclockwise relative to the proximal end of the spacer.

12. A driver for an expandable interbody spacer having a proximal end and a distal end, comprising:

a first drive portion having a first length extending along a longitudinal axis of the driver; the first drive portion having a first diameter and a non-circular cross-sectional first shape taken perpendicular to the longitudinal axis extending along the first length;

a second drive portion having a second length extending along the longitudinal axis; the second drive portion having a second diameter and a non-circular cross-sectional second shape taken perpendicular to the longitudinal axis extending along the second length;

a middle portion located between the first drive portion and the second drive portion; the middle portion having a middle length extending along the longitudinal axis; the middle portion having a middle diameter and a cross-sectional middle shape taken perpendicular to the longitudinal axis extending along the middle length;
a handle located at the proximal end; the handle having a handle length extending along the longitudinal axis and a handle diameter;
wherein the first drive portion extends from the distal end of the driver and is connected to a distal end of the middle portion; the middle portion extends from a proximal end of the first drive portion and is connected to a distal end of the second drive portion; and the handle extends from a proximal end of the second drive portion to the proximal end of the driver.

13. The driver of claim 12 wherein the first diameter and the second diameter are each a major diameter, and wherein the first and second drive portions each further comprise a minor diameter; each respective major diameter being larger than each respective minor diameter.

14. The driver of claim 12 wherein the first diameter and the second diameter are equal.

15. The driver of claim 12 wherein the first diameter and the second diameter are larger than the middle diameter.

16. The driver of claim 12 wherein the handle diameter is larger than both the first diameter and the second diameter; and both the first diameter and the second diameter are larger than the middle diameter.

17. The driver of claim 16 wherein the first diameter and the second diameter are the same.

18. The driver of claim 12 wherein the handle includes a neck portion located proximal to the second drive portion; the neck portion having a diameter smaller than the handle diameter and larger than the second diameter.

19. The driver of claim 12 wherein the first diameter is constant along the entire first length; the second diameter is constant along the entire second length; the first shape is constant along the entire first length; and the second shape is constant along the entire second length.

20. The driver of claim 12 wherein the first shape and the second shape are the same shape.

21. The driver of claim 12 wherein the middle shape is circular.

22. The driver of claim 12 wherein the middle diameter is the same as the first diameter and the second diameter, and wherein the middle shape is circular.

23. The driver of claim 12 wherein the second length is shorter than the first length.

24. A method comprising:
providing an expandable interbody spacer having a longitudinal axis, a proximal end and a distal end; the spacer including:
a housing having a threaded proximal opening and a threaded distal opening;
an upper endplate having an anterior end and a posterior end, an anterior angled surface and a posterior angled surface;
a lower endplate having an anterior end and a posterior end, an anterior angled surface and a posterior angled surface;
an anterior drive screw threadingly connected to the distal opening; the anterior drive screw having an anterior ball head connected to a threaded anterior shaft and an anterior drive bore having a bore diameter and a cross-sectional shape taken perpendicular to and extending along a longitudinal drive axis;
an anterior actuator coupled to the anterior drive screw; the anterior actuator having an upper drive surface for mating with the anterior angled surface of the upper endplate and a lower drive surface for mating with the anterior angled surface of the lower endplate;
a posterior drive screw threadingly connected to the proximal opening; the posterior drive screw having a posterior ball head connected to a threaded posterior shaft and a posterior drive bore having a bore diameter and cross-sectional shape taken perpendicular to and extending along the longitudinal drive axis; the posterior drive bore being coaxially aligned with the anterior drive bore along the longitudinal drive axis;
a posterior actuator coupled to the posterior drive screw; the posterior actuator having an upper drive surface for mating with the posterior angled surface of the upper endplate and a lower drive surface for mating with the posterior angled surface of the lower endplate;
providing a driver having a longitudinal axis, a proximal end and a distal end; the driver including:
a first drive portion having a first length extending along a longitudinal axis of the driver; the first drive portion having a first diameter and a non-circular cross-sectional first shape taken perpendicular to the longitudinal axis extending along the first length; the first shape being sized and configured to matingly engage the anterior drive bore and the posterior drive bore;
a second drive portion having a second length extending along the longitudinal axis; the second drive portion having a second diameter and a non-circular cross-sectional second shape taken perpendicular to the longitudinal axis extending along the second length; the second shape being sized and configured to matingly engage the posterior drive bore;
a middle portion located between the first drive portion and the second drive portion; the middle portion having a middle length extending along the longitudinal axis; the middle portion having a middle diameter and a cross-sectional middle shape taken perpendicular to the longitudinal axis extending along the middle length;
a handle located at the proximal end; the handle having a handle length extending along the longitudinal axis and a handle diameter;
wherein the first drive portion extends from the distal end of the driver to a distal end of the middle portion; the middle portion extends from a proximal end of the first drive portion to a distal end of the second drive portion; and the handle extends from a proximal end of the second drive portion to the proximal end of the driver.

25. The method of claim 24 further including the steps of:
inserting the driver into the anterior drive bore and the posterior drive bore from the proximal end of the spacer such that the first drive portion of the driver is located inside the anterior drive bore and the second drive portion of the driver is located inside the posterior drive bore; and
rotating the driver in a clockwise direction relative to the proximal end of the spacer to simultaneously and uniformly expand apart the anterior ends and the posterior ends of the upper and lower endplates.

26. The method of claim 25 further including the step of rotating the driver in a counterclockwise direction relative to the proximal end of the spacer to simultaneously and uniformly move the anterior ends and the posterior ends of the upper and lower endplates toward each other to reduce the distance between the upper and lower endplates.

27. The method of claim 24 further including the steps of:
inserting the driver into the anterior drive bore and the posterior drive bore from the proximal end of the spacer such that the first drive portion of the driver is located inside the anterior drive bore and the second drive portion of the driver is located proximal to the posterior drive screw and outside the posterior drive bore; and
rotating the driver in a clockwise direction relative to the proximal end of the spacer to simultaneously angulate the upper and lower endplates such that the distance between the upper and lower endplates at the distal end of the spacer increases with clockwise rotation relative to the upper and lower endplates at the proximal end of the spacer.

28. The method of claim 27 further including the step of rotating the driver in a counterclockwise direction relative to the proximal end of the spacer to simultaneously and uniformly move the anterior ends of the upper and lower endplates toward each other to reduce the distance between the upper and lower endplates at the distal end of the spacer without changing the distance between the posterior ends of the upper and lower endplates.

29. The method of claim 24 further including the steps of:
inserting the driver into the posterior drive bore from the proximal end of the spacer such that the first drive portion of the driver is located inside the posterior drive screw and the second drive portion of the driver is proximal to the posterior drive screw and outside of the spacer; and
rotating the driver in a clockwise direction relative to the proximal end of the spacer to simultaneously angulate the upper and lower endplates such that the distance between the upper and lower endplates at the proximal end of the spacer increases with clockwise rotation relative to the upper and lower endplates at the distal end of the spacer.

30. The method of claim 29 further including the step of rotating the driver in a counterclockwise direction relative to the proximal end of the spacer to simultaneously and uniformly move the posterior ends of the upper and lower endplates toward each other to reduce the distance between the upper and lower endplates at the proximal end without changing the distance between the posterior ends of the upper and lower endplates.

31. The method of claim 24 wherein the first length of the driver is equal to the length of the anterior drive screw, and the second length of the driver is shorter than the posterior drive screw.

32. The method of claim 24 wherein the spacer has a length equal to the sum of the first portion, the second portion and the middle portion.

33. The method of claim 24 wherein the middle diameter of the driver is smaller than the bore diameter of the posterior drive screw.

34. The method of claim 24 wherein the middle portion of the driver is configured not to matingly engage with the posterior drive screw.

* * * * *